US006140124A

United States Patent [19]
Monia et al.

[11] Patent Number: 6,140,124
[45] Date of Patent: Oct. 31, 2000

[54] ANTISENSE MODULATION OF P38 MITOGEN ACTIVATED PROTEIN KINASE EXPRESSION

[75] Inventors: Brett P. Monia, La Costa; William A. Gaarde, Carlsbad; Pamela S. Nero, Oceanside; Robert McKay, La Mesa, all of Calif.

[73] Assignee: Isis Pharmaceuticals Inc., Carlsbad, Calif.

[21] Appl. No.: 09/286,904

[22] Filed: Apr. 6, 1999

[51] Int. Cl.[7] .......................... C07H 21/04; C07H 21/02; C12N 5/00; C12Q 1/68
[52] U.S. Cl. ........................ 435/375; 536/23.1; 536/24.3; 536/24.31; 536/24.33; 536/24.5; 435/6; 435/91.1; 435/325
[58] Field of Search .................................. 536/24.5, 23.1; 435/91.1, 6; 514/44

[56] References Cited

U.S. PATENT DOCUMENTS

| | | | |
|---|---|---|---|
| 5,652,355 | 7/1997 | Metelev et al. | 536/24.5 |
| 5,856,462 | 1/1999 | Agrawal | 536/24.5 |

OTHER PUBLICATIONS

Aoshiba et al., "Role of p38–Mitogen–Activated Protein Kinase in Spontaneous Apoptosis of Human Neutrophils", J. Immunol., 1999, 162, 1692–1700.

Cohen et al., "The Critical Role of p38 MAP Kinase in T Cell HIV–1 Replication", Mol. Med., 1997, 3, 339–346.

Nagata et al., "Activation of p38 MAP Kinase and JNK But Not ERK Is Required for Erythropoietin–Induced Erythroid Differentiation", Blood, 1998, 6, 1859–1869.

Andrea D. Branch, A good antisense molecule is hard to find, TIBS, 47–48, Feb. 1998.

Trisha Gura, Antisense Has Growing Pains, Science, pp. 575–577, Oct. 1995.

Stanley Crooke, Antisense Research and Applications, Chapter 1, Basic Principles of Antisense Therapeutics, Springer–Verlag Press, Berlin, Heidelberg, New York, p. 3, Jul. 1998.

*Primary Examiner*—George C. Elliott
*Assistant Examiner*—Janet L Epps
*Attorney, Agent, or Firm*—Law Offices of Jane Massey Licata

[57] ABSTRACT

Compositions and methods for the treatment and diagnosis of diseases or conditions amenable to treatment through modulation of expression of a gene encoding a p38 mitogen-activated protein kinase (p38 MAPK) are provided. Methods for the treatment and diagnosis of diseases or conditions associated with aberrant expression of one or more p38 MAPKs are also provided.

24 Claims, No Drawings

SEQUENCE LISTING

<160> NUMBER OF SEQ ID NOS: 95

<210> SEQ ID NO 1
<211> LENGTH: 1539
<212> TYPE: DNA
<213> ORGANISM: Homo sapiens
<220> FEATURE:
<221> NAME/KEY: CDS
<222> LOCATION: (295)..(1377)
<300> PUBLICATION INFORMATION:
<303> JOURNAL: Science
<304> VOLUME: 265
<305> ISSUE: 5173
<306> PAGES: 808-811
<307> DATE: 1994-08-05
<308> DATABASE ACCESSION NUMBER: L35253
<309> DATABASE ENTRY DATE: 1995-08-14

<400> SEQUENCE: 1
ggaattccgg gcccggtctt tcctcccgcc gccgccggcc tggtcccggg gactggcctc        60
cacgtccgac tcgtccgagc tgaagcccag cagcactttg ctgccagccg cggggcggc        120 ggaggcgccc ccgggccctc ccaggaggct ctctgggcca gaggccgaga ttcggcacag       180
gcccccagga gtccgtaagt aggagaggtc gcccgagacc ggccggaccc ccatccccgc       240

-continued

| | |
|---|---|
| ggccgccgcc gccgctggtc ccgcggctgc gaccgtggcg gctgccgctg gaaa atg<br>                                                                                                                                                              Met<br>                                                                                                                                                              1 | 297 |
| tct cag gag agg ccc acg ttc tac cgg cag gag ctg aac aag aca atc<br>Ser Gln Glu Arg Pro Thr Phe Tyr Arg Gln Glu Leu Asn Lys Thr Ile<br>                5                          10                         15 | 345 |
| tgg gag gtg ccc gag cgt tac cag aac ctg tct cca gtg ggc tct ggc<br>Trp Glu Val Pro Glu Arg Tyr Gln Asn Leu Ser Pro Val Gly Ser Gly<br>                20                         25                         30 | 393 |
| gcc tat ggc tct gtg tgt gct gct ttt gac aca aaa acg ggg tta cgt<br>Ala Tyr Gly Ser Val Cys Ala Ala Phe Asp Thr Lys Thr Gly Leu Arg<br>35                    40                         45 | 441 |
| gtg gca gtg aag aag ctc tcc aga cca ttt cag tcc atc att cat gcg<br>Val Ala Val Lys Lys Leu Ser Arg Pro Phe Gln Ser Ile Ile His Ala<br>50                    55                         60                       65 | 489 |
| aaa aga acc tac aga gaa ctg cgg tta ctt aaa cat atg aaa cat gaa<br>Lys Arg Thr Tyr Arg Glu Leu Arg Leu Leu Lys His Met Lys His Glu<br>                70                         75                         80 | 537 |
| aat gtg att ggt ctg ttg gac gtt ttt aca cct gca agg tct ctg gag<br>Asn Val Ile Gly Leu Leu Asp Val Phe Thr Pro Ala Arg Ser Leu Glu<br>                  85                         90                       95 | 585 |
| gaa ttc aat gat gtg tat ctg gtg acc cat ctc atg ggg gca gat ctg<br>Glu Phe Asn Asp Val Tyr Leu Val Thr His Leu Met Gly Ala Asp Leu<br>                100                      105                      110 | 633 |
| aac aac att gtg aaa tgt cag aag ctt aca gat gac cat gtt cag ttc<br>Asn Asn Ile Val Lys Cys Gln Lys Leu Thr Asp Asp His Val Gln Phe<br>115                   120                       125 | 681 |
| ctt atc tac caa att ctc cga ggt cta aag tat ata cat tca gct gac<br>Leu Ile Tyr Gln Ile Leu Arg Gly Leu Lys Tyr Ile His Ser Ala Asp<br>130                   135                       140                       145 | 729 |
| ata att cac agg gac cta aaa cct agt aat cta gct gtg aat gaa gac<br>Ile Ile His Arg Asp Leu Lys Pro Ser Asn Leu Ala Val Asn Glu Asp<br>                150                      155                      160 | 777 |
| tgt gag ctg aag att ctg gat ttt gga ctg gct cgg cac aca gat gat<br>Cys Glu Leu Lys Ile Leu Asp Phe Gly Leu Ala Arg His Thr Asp Asp<br>                165                      170                      175 | 825 |
| gaa atg aca ggc tac gtg gcc act agg tgg tac agg gct cct gag atc<br>Glu Met Thr Gly Tyr Val Ala Thr Arg Trp Tyr Arg Ala Pro Glu Ile<br>180                   185                       190 | 873 |
| atg ctg aac tgg atg cat tac aac cag aca gtt gat att tgg tca gtg<br>Met Leu Asn Trp Met His Tyr Asn Gln Thr Val Asp Ile Trp Ser Val<br>195                 200                       205 | 921 |
| gga tgc ata atg gcc gag ctg ttg act gga aga aca ttg ttt cct ggt<br>Gly Cys Ile Met Ala Glu Leu Leu Thr Gly Arg Thr Leu Phe Pro Gly<br>210                   215                       220                       225 | 969 |
| aca gac cat att gat cag ttg aag ctc att tta aga ctc gtt gga acc<br>Thr Asp His Ile Asp Gln Leu Lys Leu Ile Leu Arg Leu Val Gly Thr<br>                230                      235                      240 | 1017 |
| cca ggg gct gag ctt ttg aag aaa atc tcc tca gag tct gca aga aac<br>Pro Gly Ala Glu Leu Leu Lys Lys Ile Ser Ser Glu Ser Ala Arg Asn<br>                  245                      250                      255 | 1065 |
| tat att cag tct ttg act cag atg ccg aag atg aac ttt gcg aat gta<br>Tyr Ile Gln Ser Leu Thr Gln Met Pro Lys Met Asn Phe Ala Asn Val<br>                260                      265                      270 | 1113 |
| ttt att ggt gcc aat ccc ctg gct gtc gac ttg ctg gag aag atg ctt<br>Phe Ile Gly Ala Asn Pro Leu Ala Val Asp Leu Leu Glu Lys Met Leu<br>275                   280                       285 | 1161 |
| gta ttg gac tca gat aag aga att aca gcg gcc caa gcc ctt gca cat<br>Val Leu Asp Ser Asp Lys Arg Ile Thr Ala Ala Gln Ala Leu Ala His<br>290                   295                       300                      305 | 1209 |

```
gcc tac ttt gct cag tac cac gat cct gat gat gaa cca gtg gcc gat      1257
Ala Tyr Phe Ala Gln Tyr His Asp Pro Asp Asp Glu Pro Val Ala Asp
                310                 315                 320 cct tat gat cag tcc ttt gaa agc agg gac ctc ctt ata gat gag tgg      1305
Pro Tyr Asp Gln Ser Phe Glu Ser Arg Asp Leu Leu Ile Asp Glu Trp
            325                 330                 335 aaa agc ctg acc tat gat gaa gtc atc agc ttt gtg cca cca ccc ctt      1353
Lys Ser Leu Thr Tyr Asp Glu Val Ile Ser Phe Val Pro Pro Pro Leu
        340                 345                 350 gac caa gaa gag atg gag tcc tga gcacctggtt tctgttctgt tgatcccact     1407
Asp Gln Glu Glu Met Glu Ser
    355                 360 tcactgtgag gggaaggcct tttcacggga actctccaaa tattattcaa gtgcctcttg    1467
ttgcagagat ttcctccatg gtggaagggg gtgtgcgtgc gtgtgcgtgc gtgttagtgt    1527
gtgtgcatgt gt                                                        1539

<210> SEQ ID NO 2
<211> LENGTH: 360
<212> TYPE: PRT
<213> ORGANISM: Homo sapiens

<400> SEQUENCE: 2

Met Ser Gln Glu Arg Pro Thr Phe Tyr Arg Gln Glu Leu Asn Lys Thr
 1               5                  10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
    210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255
```

```
Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
    290                 295                 300

His Ala Tyr Phe Ala Gln Tyr His Asp Pro Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
                340                 345                 350

Leu Asp Gln Glu Glu Met Glu Ser
                355                 360
```

<210> SEQ ID NO 3
<211> LENGTH: 20
<212> TYPE: DNA
<213> ORGANISM: Artificial Sequence
<220> FEATURE:
<223> OTHER INFORMATION: antisense sequence

<400> SEQUENCE: 3
aagaccgggc ccggaattcc                                              20

<210> SEQ ID NO 4
<211> LENGTH: 30
<212> TYPE: DNA
<213> ORGANISM: Artificial Sequence
<220> FEATURE:
<223> OTHER INFORMATION: antisense sequence

<400> SEQUENCE: 4
gtggaggcca gtccccggga ccggaattcc                                   30

<210> SEQ ID NO 5
<211> LENGTH: 20
<212> TYPE: DNA
<213> ORGANISM: Artificial Sequence
<220> FEATURE:
<223> OTHER INFORMATION: antisense sequence

<400> SEQUENCE: 5
tggcagcaaa gtgctgctgg                                              20

<210> SEQ ID NO 6
<211> LENGTH: 20
<212> TYPE: DNA
<213> ORGANISM: Artificial Sequence
<220> FEATURE:
<223> OTHER INFORMATION: antisense sequence

<400> SEQUENCE: 6
cagagagcct cctgggaggg                                              20

<210> SEQ ID NO 7
<211> LENGTH: 20
<212> TYPE: DNA
<213> ORGANISM: Artificial Sequence
<220> FEATURE:
<223> OTHER INFORMATION: antisense sequence

<400> SEQUENCE: 7
tgtgccgaat ctcggcctct                                                           20

<210> SEQ ID NO 8
<211> LENGTH: 20
<212> TYPE: DNA
<213> ORGANISM: Artificial Sequence
<220> FEATURE:
<223> OTHER INFORMATION: antisense sequence

<400> SEQUENCE: 8
ggtctcgggc gacctctcct                                                           20

<210> SEQ ID NO 9
<211> LENGTH: 20
<212> TYPE: DNA
<213> ORGANISM: Artificial Sequence
<220> FEATURE:
<223> OTHER INFORMATION: antisense sequence

<400> SEQUENCE: 9
cagccgcggg accagcggcg                                                           20

<210> SEQ ID NO 10
<211> LENGTH: 20
<212> TYPE: DNA
<213> ORGANISM: Artificial Sequence
<220> FEATURE:
<223> OTHER INFORMATION: antisense sequence

<400> SEQUENCE: 10
cattttccag cggcagccgc                                                           20

<210> SEQ ID NO 11
<211> LENGTH: 20
<212> TYPE: DNA
<213> ORGANISM: Artificial Sequence
<220> FEATURE:
<223> OTHER INFORMATION: antisense sequence

<400> SEQUENCE: 11
tcctgagaca ttttccagcg                                                           20

<210> SEQ ID NO 12
<211> LENGTH: 20
<212> TYPE: DNA
<213> ORGANISM: Artificial Sequence
<220> FEATURE:
<223> OTHER INFORMATION: antisense sequence

<400> SEQUENCE: 12
ctgccggtag aacgtgggcc                                                           20

<210> SEQ ID NO 13
<211> LENGTH: 20
<212> TYPE: DNA
<213> ORGANISM: Artificial Sequence
<220> FEATURE:
<223> OTHER INFORMATION: antisense sequence

<400> SEQUENCE: 13
gtaagcttct gacatttcac                                                           20

```
<210> SEQ ID NO 14
<211> LENGTH: 20
<212> TYPE: DNA
<213> ORGANISM: Artificial Sequence
<220> FEATURE:
<223> OTHER INFORMATION: antisense sequence

<400> SEQUENCE: 14
tttaggtccc tgtgaattat                                               20

<210> SEQ ID NO 15
<211> LENGTH: 20
<212> TYPE: DNA
<213> ORGANISM: Artificial Sequence
<220> FEATURE:
<223> OTHER INFORMATION: antisense sequence

<400> SEQUENCE: 15
atgttcttcc agtcaacagc                                               20

<210> SEQ ID NO 16
<211> LENGTH: 20
<212> TYPE: DNA
<213> ORGANISM: Artificial Sequence
<220> FEATURE:
<223> OTHER INFORMATION: antisense sequence

<400> SEQUENCE: 16
taaggaggtc cctgctttca                                               20

<210> SEQ ID NO 17
<211> LENGTH: 20
<212> TYPE: DNA
<213> ORGANISM: Artificial Sequence
<220> FEATURE:
<223> OTHER INFORMATION: antisense sequence

<400> SEQUENCE: 17
aaccaggtgc tcaggactcc                                               20

<210> SEQ ID NO 18
<211> LENGTH: 20
<212> TYPE: DNA
<213> ORGANISM: Artificial Sequence
<220> FEATURE:
<223> OTHER INFORMATION: antisense sequence

<400> SEQUENCE: 18
gaagtgggat caacagaaca                                               20

<210> SEQ ID NO 19
<211> LENGTH: 20
<212> TYPE: DNA
<213> ORGANISM: Artificial Sequence
<220> FEATURE:
<223> OTHER INFORMATION: antisense sequence

<400> SEQUENCE: 19
tgaaaaggcc ttccccctcac                                              20

<210> SEQ ID NO 20
<211> LENGTH: 20
<212> TYPE: DNA
<213> ORGANISM: Artificial Sequence
<220> FEATURE:
<223> OTHER INFORMATION: antisense sequence
```

-continued

```
<400> SEQUENCE: 20
aggcacttga ataatatttg                                                        20

<210> SEQ ID NO 21
<211> LENGTH: 20
<212> TYPE: DNA
<213> ORGANISM: Artificial Sequence
<220> FEATURE:
<223> OTHER INFORMATION: antisense sequence

<400> SEQUENCE: 21
cttccaccat ggaggaaatc                                                        20

<210> SEQ ID NO 22
<211> LENGTH: 20
<212> TYPE: DNA
<213> ORGANISM: Artificial Sequence
<220> FEATURE:
<223> OTHER INFORMATION: antisense sequence

<400> SEQUENCE: 22
acacatgcac acacactaac                                                        20

<210> SEQ ID NO 23
<211> LENGTH: 2180
<212> TYPE: DNA
<213> ORGANISM: Homo sapiens
<220> FEATURE:
<221> NAME/KEY: CDS
<222> LOCATION: (20)..(1138)
<300> PUBLICATION INFORMATION:
<308> DATABASE ACCESSION NUMBER: U53442
<309> DATABASE ENTRY DATE: 1996-07-30

<400> SEQUENCE: 23
gtgaaattct gctccggac atg tcg ggc cct cgc gcc ggc ttc tac cgg cag            52
                    Met Ser Gly Pro Arg Ala Gly Phe Tyr Arg Gln
                     1               5                  10 gag ctg aac aag acc gtg tgg gag gtg ccg cag cgg ctg cag ggg ctg            100
Glu Leu Asn Lys Thr Val Trp Glu Val Pro Gln Arg Leu Gln Gly Leu
         15                  20                  25 cgc ccg gtg ggc tcc ggc gcc tac ggc tcc gtc tgt tcg gcc tac gac            148
Arg Pro Val Gly Ser Gly Ala Tyr Gly Ser Val Cys Ser Ala Tyr Asp
     30                  35                  40 gcc cgg ctg cgc cag aag gtg gcg gtg aag aag ctg tcg cgc ccc ttc            196
Ala Arg Leu Arg Gln Lys Val Ala Val Lys Lys Leu Ser Arg Pro Phe
 45                  50                  55 cag tcg ctg atc cac gcg cgc aga acg tac cgg gag ctg cgg ctg ctc            244
Gln Ser Leu Ile His Ala Arg Arg Thr Tyr Arg Glu Leu Arg Leu Leu
 60                  65                  70                  75 aag cac ctg aag cac gag aac gtc atc ggg ctt ctg gac gtc ttc acg            292
Lys His Leu Lys His Glu Asn Val Ile Gly Leu Leu Asp Val Phe Thr
                 80                  85                  90 ccg gcc acg tcc atc gag gac ttc agc gaa gtg tac ttg gtg acc acc            340
Pro Ala Thr Ser Ile Glu Asp Phe Ser Glu Val Tyr Leu Val Thr Thr
             95                 100                 105 ctg atg ggc gcc gac ctg aac aac atc gtc aag tgc cag gcg ggc gcc            388
Leu Met Gly Ala Asp Leu Asn Asn Ile Val Lys Cys Gln Ala Gly Ala
        110                 115                 120 cat cag ggt gcc cgc ctg gca ctt gac gag cac gtt caa ttc ctg gtt            436
His Gln Gly Ala Arg Leu Ala Leu Asp Glu His Val Gln Phe Leu Val
    125                 130                 135
```

-continued

| | |
|---|---|
| tac cag ctg ctg cgc ggg ctg aag tac atc cac tcg gcc ggg atc atc<br>Tyr Gln Leu Leu Arg Gly Leu Lys Tyr Ile His Ser Ala Gly Ile Ile<br>140                      145                    150                 155 | 484 |
| cac cgg gac ctg aag ccc agc aac gtg gct gtg aac gag gac tgt gag<br>His Arg Asp Leu Lys Pro Ser Asn Val Ala Val Asn Glu Asp Cys Glu<br>                    160                    165                    170 | 532 |
| ctc agg atc ctg gat ttc ggg ctg gcg cgc cag gcg gac gag gag atg<br>Leu Arg Ile Leu Asp Phe Gly Leu Ala Arg Gln Ala Asp Glu Glu Met<br>          175                    180                    185 | 580 |
| acc ggc tat gtg gcc acg cgc tgg tac cgg gca cct gag atc atg ctc<br>Thr Gly Tyr Val Ala Thr Arg Trp Tyr Arg Ala Pro Glu Ile Met Leu<br>190                      195                    200 | 628 |
| aac tgg atg cat tac aac caa aca gtg gat atc tgg tcc gtg ggc tgc<br>Asn Trp Met His Tyr Asn Gln Thr Val Asp Ile Trp Ser Val Gly Cys<br>    205                    210                    215 | 676 |
| atc atg gct gag ctg ctc cag ggc aag gcc ctc ttc ccg gga agc gac<br>Ile Met Ala Glu Leu Leu Gln Gly Lys Ala Leu Phe Pro Gly Ser Asp<br>220                      225                    230                    235 | 724 |
| tac att gac cag ctg aag cgc atc atg gaa gtg gtg ggc aca ccc agc<br>Tyr Ile Asp Gln Leu Lys Arg Ile Met Glu Val Val Gly Thr Pro Ser<br>                    240                    245                    250 | 772 |
| cct gag gtt ctg gca aaa atc tcc tcg gaa cac gcc cgg aca tat atc<br>Pro Glu Val Leu Ala Lys Ile Ser Ser Glu His Ala Arg Thr Tyr Ile<br>          255                    260                    265 | 820 |
| cag tcc ctg ccc ccc atg ccc cag aag gac ctg agc agc atc ttc cgt<br>Gln Ser Leu Pro Pro Met Pro Gln Lys Asp Leu Ser Ser Ile Phe Arg<br>                    270                    275                    280 | 868 |
| gga gcc aac ccc ctg gcc ata gac ctc ctt gga agg atg ctg gtg ctg<br>Gly Ala Asn Pro Leu Ala Ile Asp Leu Leu Gly Arg Met Leu Val Leu<br>    285                    290                    295 | 916 |
| gac agt gac cag agg gtc agt gca gct gag gca ctg gcc cac gcc tac<br>Asp Ser Asp Gln Arg Val Ser Ala Ala Glu Ala Leu Ala His Ala Tyr<br>300                      305                    310                 315 | 964 |
| ttc agc cag tac cac gac ccc gag gat gag cca gag gcc gag cca tat<br>Phe Ser Gln Tyr His Asp Pro Glu Asp Glu Pro Glu Ala Glu Pro Tyr<br>                    320                    325                    330 | 1012 |
| gat gag agc gtt gag gcc aag gag cgc acg ctg gag gag tgg aag gag<br>Asp Glu Ser Val Glu Ala Lys Glu Arg Thr Leu Glu Glu Trp Lys Glu<br>          335                    340                    345 | 1060 |
| ctc act tac cag gaa gtc ctt agc ttc aag ccc cca gag cca ccg aag<br>Leu Thr Tyr Gln Glu Val Leu Ser Phe Lys Pro Pro Glu Pro Pro Lys<br>                    350                    355                    360 | 1108 |
| cca cct ggc agc ctg gag att gag cag tga ggtgctgccc agcagcccct<br>Pro Pro Gly Ser Leu Glu Ile Glu Gln<br>    365                    370 | 1158 |
| gagagcctgt ggagggcctt gggcctgcac ccttccacag ctggcctggt ttcctcgaga | 1218 |
| ggcacctccc acactcctat ggtcacagac ttctggccta ggacccctcg ccttcaggag | 1278 |
| aatctacacg catgtatgca tgcacaaaca tgtgtgtaca tgtgcttgcc atgtgtagga | 1338 |
| gtctgggcac aagtgtccct gggcctacct tggtcctcct gtcctcttct ggctactgca | 1398 |
| ctctccactg ggacctgact gtgggtcct agatgccaaa ggggttcccc tgcggagttc | 1458 |
| ccctgtctgt cccaggccga cccaaggag tgtcagcctt gggctctctt ctgtcccagg | 1518 |
| gctttctgga gggcgcgctg gggccgggac cccgggagac tcaaagggag aggtctcagt | 1578 |
| ggttagagct gctcagcctg gaggtagggc gctgtcttgg tcactgctga gacccacagg | 1638 |
| tctaagagga gaggcagagc cagtgtgcca ccaggctggg cagggacaac caccaggtgt | 1698 |
| caaatgagaa aagctgcctg gagtcttgtg ttcacccgtg ggtgtgtgtg ggcacgtgtg | 1758 |

-continued

```
gatgagcgtg cactccccgt gttcatatgt cagggcacat gtgatgtggt gcgtgtgaat    1818
ctgtgggcgc ccaaggccag cagccatatc tggcaagaag ctggagccgg ggtgggtgtg    1878
ctgttgcctt ccctctcctc ggttcctgat gccttgaggg gtgtttcaga ctggcggcac    1938
cgttgtggcc ctgcagccgg agatctgagg tgctctggtc tgtgggtcag tcctctttcc    1998
ttgtcccagg atgagctga tccagtaacc tcggagacgg gaccctgccc agagctgagt     2058
tgggggtgtg gctctgccct ggaaaggggg tgacctcttg cctcgagggg cccagggaag    2118
cctgggtgtc aagtgcctgc accagggtg cacaataaag ggggttctct ctcagaaaaa     2178
aa                                                                    2180
```

<210> SEQ ID NO 24
<211> LENGTH: 372
<212> TYPE: PRT
<213> ORGANISM: Homo sapiens

<400> SEQUENCE: 24

```
Met Ser Gly Pro Arg Ala Gly Phe Tyr Arg Gln Glu Leu Asn Lys Thr
  1               5                  10                  15

Val Trp Glu Val Pro Gln Arg Leu Gln Gly Leu Arg Pro Val Gly Ser
                 20                  25                  30

Gly Ala Tyr Gly Ser Val Cys Ser Ala Tyr Asp Ala Arg Leu Arg Gln
             35                  40                  45

Lys Val Ala Val Lys Lys Leu Ser Arg Pro Phe Gln Ser Leu Ile His
         50                  55                  60

Ala Arg Arg Thr Tyr Arg Glu Leu Arg Leu Leu Lys His Leu Lys His
  65                  70                  75                  80

Glu Asn Val Ile Gly Leu Leu Asp Val Phe Thr Pro Ala Thr Ser Ile
                 85                  90                  95

Glu Asp Phe Ser Glu Val Tyr Leu Val Thr Thr Leu Met Gly Ala Asp
            100                 105                 110

Leu Asn Asn Ile Val Lys Cys Gln Ala Gly Ala His Gln Gly Ala Arg
        115                 120                 125

Leu Ala Leu Asp Glu His Val Gln Phe Leu Val Tyr Gln Leu Leu Arg
    130                 135                 140

Gly Leu Lys Tyr Ile His Ser Ala Gly Ile Ile His Arg Asp Leu Lys
145                 150                 155                 160

Pro Ser Asn Val Ala Val Asn Glu Asp Cys Glu Leu Arg Ile Leu Asp
                165                 170                 175

Phe Gly Leu Ala Arg Gln Ala Asp Glu Glu Met Thr Gly Tyr Val Ala
            180                 185                 190

Thr Arg Trp Tyr Arg Ala Pro Glu Ile Met Leu Asn Trp Met His Tyr
        195                 200                 205

Asn Gln Thr Val Asp Ile Trp Ser Val Gly Cys Ile Met Ala Glu Leu
    210                 215                 220

Leu Gln Gly Lys Ala Leu Phe Pro Gly Ser Asp Tyr Ile Asp Gln Leu
225                 230                 235                 240

Lys Arg Ile Met Glu Val Val Gly Thr Pro Ser Pro Glu Val Leu Ala
                245                 250                 255

Lys Ile Ser Ser Glu His Ala Arg Thr Tyr Ile Gln Ser Leu Pro Pro
            260                 265                 270

Met Pro Gln Lys Asp Leu Ser Ser Ile Phe Arg Gly Ala Asn Pro Leu
        275                 280                 285
```

```
Ala Ile Asp Leu Leu Gly Arg Met Leu Val Leu Asp Ser Asp Gln Arg
    290                 295                 300

Val Ser Ala Ala Glu Ala Leu Ala His Ala Tyr Phe Ser Gln Tyr His
305                 310                 315                 320

Asp Pro Glu Asp Glu Pro Glu Ala Glu Pro Tyr Asp Glu Ser Val Glu
                325                 330                 335

Ala Lys Glu Arg Thr Leu Glu Glu Trp Lys Glu Leu Thr Tyr Gln Glu
                340                 345                 350

Val Leu Ser Phe Lys Pro Pro Glu Pro Pro Lys Pro Pro Gly Ser Leu
                355                 360                 365

Glu Ile Glu Gln
    370

<210> SEQ ID NO 25
<211> LENGTH: 20
<212> TYPE: DNA
<213> ORGANISM: Artificial Sequence
<220> FEATURE:
<223> OTHER INFORMATION: antisense sequence

<400> SEQUENCE: 25
cgacatgtcc ggagcagaat                                              20

<210> SEQ ID NO 26
<211> LENGTH: 20
<212> TYPE: DNA
<213> ORGANISM: Artificial Sequence
<220> FEATURE:
<223> OTHER INFORMATION: antisense sequence

<400> SEQUENCE: 26
ttcagctcct gccggtagaa                                              20

<210> SEQ ID NO 27
<211> LENGTH: 20
<212> TYPE: DNA
<213> ORGANISM: Artificial Sequence
<220> FEATURE:
<223> OTHER INFORMATION: antisense sequence

<400> SEQUENCE: 27
tgcggcacct cccacacggt                                              20

<210> SEQ ID NO 28
<211> LENGTH: 20
<212> TYPE: DNA
<213> ORGANISM: Artificial Sequence
<220> FEATURE:
<223> OTHER INFORMATION: antisense sequence

<400> SEQUENCE: 28
ccgaacagac ggagccgtat                                              20

<210> SEQ ID NO 29
<211> LENGTH: 20
<212> TYPE: DNA
<213> ORGANISM: Artificial Sequence
<220> FEATURE:
<223> OTHER INFORMATION: antisense sequence
```

```
<400> SEQUENCE: 29
gtgcttcagg tgcttgagca                                             20

<210> SEQ ID NO 30
<211> LENGTH: 20
<212> TYPE: DNA
<213> ORGANISM: Artificial Sequence
<220> FEATURE:
<223> OTHER INFORMATION: antisense sequence

<400> SEQUENCE: 30
gcgtgaagac gtccagaagc                                             20

<210> SEQ ID NO 31
<211> LENGTH: 20
<212> TYPE: DNA
<213> ORGANISM: Artificial Sequence
<220> FEATURE:
<223> OTHER INFORMATION: antisense sequence

<400> SEQUENCE: 31
acttgacgat gttgttcagg                                             20

<210> SEQ ID NO 32
<211> LENGTH: 20
<212> TYPE: DNA
<213> ORGANISM: Artificial Sequence
<220> FEATURE:
<223> OTHER INFORMATION: antisense sequence

<400> SEQUENCE: 32
aacgtgctcg tcaagtgcca                                             20

<210> SEQ ID NO 33
<211> LENGTH: 20
<212> TYPE: DNA
<213> ORGANISM: Artificial Sequence
<220> FEATURE:
<223> OTHER INFORMATION: antisense sequence

<400> SEQUENCE: 33
atcctgagct cacagtcctc                                             20

<210> SEQ ID NO 34
<211> LENGTH: 20
<212> TYPE: DNA
<213> ORGANISM: Artificial Sequence
<220> FEATURE:
<223> OTHER INFORMATION: antisense sequence

<400> SEQUENCE: 34
actgtttggt tgtaatgcat                                             20

<210> SEQ ID NO 35
<211> LENGTH: 20
<212> TYPE: DNA
<213> ORGANISM: Artificial Sequence
<220> FEATURE:
<223> OTHER INFORMATION: antisense sequence

<400> SEQUENCE: 35
atgatgcgct tcagctggtc                                             20
```

```
<210> SEQ ID NO 36
<211> LENGTH: 20
<212> TYPE: DNA
<213> ORGANISM: Artificial Sequence
<220> FEATURE:
<223> OTHER INFORMATION: antisense sequence

<400> SEQUENCE: 36
gccagtgcct cagctgcact                                                    20

<210> SEQ ID NO 37
<211> LENGTH: 20
<212> TYPE: DNA
<213> ORGANISM: Artificial Sequence
<220> FEATURE:
<223> OTHER INFORMATION: antisense sequence

<400> SEQUENCE: 37
aacgctctca tcatatggct                                                    20

<210> SEQ ID NO 38
<211> LENGTH: 20
<212> TYPE: DNA
<213> ORGANISM: Artificial Sequence
<220> FEATURE:
<223> OTHER INFORMATION: antisense sequence

<400> SEQUENCE: 38
cagcacctca ctgctcaatc                                                    20

<210> SEQ ID NO 39
<211> LENGTH: 20
<212> TYPE: DNA
<213> ORGANISM: Artificial Sequence
<220> FEATURE:
<223> OTHER INFORMATION: antisense sequence

<400> SEQUENCE: 39
tctgtgacca taggagtgtg                                                    20

<210> SEQ ID NO 40
<211> LENGTH: 20
<212> TYPE: DNA
<213> ORGANISM: Artificial Sequence
<220> FEATURE:
<223> OTHER INFORMATION: antisense sequence

<400> SEQUENCE: 40
acacatgttt gtgcatgcat                                                    20

<210> SEQ ID NO 41
<211> LENGTH: 20
<212> TYPE: DNA
<213> ORGANISM: Artificial Sequence
<220> FEATURE:
<223> OTHER INFORMATION: antisense sequence

<400> SEQUENCE: 41
cctacacatg gcaagcacat                                                    20

<210> SEQ ID NO 42
<211> LENGTH: 20
<212> TYPE: DNA
<213> ORGANISM: Artificial Sequence
<220> FEATURE:
<223> OTHER INFORMATION: antisense sequence
```

```
<400> SEQUENCE: 42
tccaggctga gcagctctaa                                                     20

<210> SEQ ID NO 43
<211> LENGTH: 20
<212> TYPE: DNA
<213> ORGANISM: Artificial Sequence
<220> FEATURE:
<223> OTHER INFORMATION: antisense sequence

<400> SEQUENCE: 43
agtgcacgct catccacacg                                                     20

<210> SEQ ID NO 44
<211> LENGTH: 20
<212> TYPE: DNA
<213> ORGANISM: Artificial Sequence
<220> FEATURE:
<223> OTHER INFORMATION: antisense sequence

<400> SEQUENCE: 44
cttgccagat atggctgctg                                                     20

<210> SEQ ID NO 45
<211> LENGTH: 3132
<212> TYPE: DNA
<213> ORGANISM: Rattus norvegicus
<220> FEATURE:
<221> NAME/KEY: CDS
<222> LOCATION: (12)..(1094)
<300> PUBLICATION INFORMATION:
<308> DATABASE ACCESSION NUMBER: U73142
<309> DATABASE ENTRY DATE: 1996-10-22

<400> SEQUENCE: 45
```

| | | | | | | | | | | | | |
|---|---|---|---|---|---|---|---|---|---|---|---|---|
| gccgctggaa a | atg | tcg | cag | gaa | agg | ccc | acg | ttc | tac | cgg | cag | gag ctg | 50 |
| | Met | Ser | Gln | Glu | Arg | Pro | Thr | Phe | Tyr | Arg | Gln | Glu Leu | |
| | 1 | | | 5 | | | | | 10 | | | | |

| aac | aag | acc | gtc | tgg | gag | gtg | ccc | gag | cga | tac | cag | aac | ctg | tcc | ccg | 98 |
|---|---|---|---|---|---|---|---|---|---|---|---|---|---|---|---|---|
| Asn | Lys | Thr | Val | Trp | Glu | Val | Pro | Glu | Arg | Tyr | Gln | Asn | Leu | Ser | Pro | |
| 15 | | | | | 20 | | | | | 25 | | | | | | | gtg ggc tcg gga gcc tac ggc tcg gtg tgt gct gct ttt gat aca aag    146
Val Gly Ser Gly Ala Tyr Gly Ser Val Cys Ala Ala Phe Asp Thr Lys
     30              35              40              45 acg gga cat cgt gtg gca gtg aag aag ctg tcg aga ccg ttt cag tcc    194
Thr Gly His Arg Val Ala Val Lys Lys Leu Ser Arg Pro Phe Gln Ser
         50              55              60 atc att cac gcc aaa agg acc tac agg gag ctg cgg ctg ctg aag cac    242
Ile Ile His Ala Lys Arg Thr Tyr Arg Glu Leu Arg Leu Leu Lys His
     65              70              75 atg aag cac gag aat gtg att ggt ctg ttg gat gtg ttt aca cct gca    290
Met Lys His Glu Asn Val Ile Gly Leu Leu Asp Val Phe Thr Pro Ala
 80              85              90 agg tcc ctg gaa gaa ttc aac gat gtg tac ctg gtg acc cat ctc atg    338
Arg Ser Leu Glu Glu Phe Asn Asp Val Tyr Leu Val Thr His Leu Met
     95              100             105 ggg gca gac ctg aac aac atc gtg aag tgt cag aag ctt acc gat gac    386
Gly Ala Asp Leu Asn Asn Ile Val Lys Cys Gln Lys Leu Thr Asp Asp
110             115             120             125 cac gtt cag ttt ctt atc tac cag atc ctg cga ggg ctg aag tat ata    434
His Val Gln Phe Leu Ile Tyr Gln Ile Leu Arg Gly Leu Lys Tyr Ile
             130             135             140

-continued

| | |
|---|---|
| cac tcg gct gac ata atc cac agg gac cta aag ccc agc aac ctc gct<br>His Ser Ala Asp Ile Ile His Arg Asp Leu Lys Pro Ser Asn Leu Ala<br>                145                  150                155 | 482 |
| gtg aat gaa gac tgt gag ctg aag att ctg gat ttt ggg ctg gct cgg<br>Val Asn Glu Asp Cys Glu Leu Lys Ile Leu Asp Phe Gly Leu Ala Arg<br>160                  165                  170 | 530 |
| cac act gat gac gaa atg acc ggc tac gtg gct acc cgg tgg tac aga<br>His Thr Asp Asp Glu Met Thr Gly Tyr Val Ala Thr Arg Trp Tyr Arg<br>175                  180                  185 | 578 |
| gcc ccc gag att atg ctg aat tgg atg cac tac aac cag aca gtg gat<br>Ala Pro Glu Ile Met Leu Asn Trp Met His Tyr Asn Gln Thr Val Asp<br>190                  195                  200              205 | 626 |
| att tgg tcc gtg ggc tgc atc atg gct gag ctg ttg acc gga aga acg<br>Ile Trp Ser Val Gly Cys Ile Met Ala Glu Leu Leu Thr Gly Arg Thr<br>                210                  215                  220 | 674 |
| ttg ttt cct ggt aca gac cat att gat cag ttg aag ctc att tta aga<br>Leu Phe Pro Gly Thr Asp His Ile Asp Gln Leu Lys Leu Ile Leu Arg<br>                225                  230                  235 | 722 |
| ctc gtt gga acc cca ggg gct gag ctt ctg aag aaa atc tcc tca gag<br>Leu Val Gly Thr Pro Gly Ala Glu Leu Leu Lys Lys Ile Ser Ser Glu<br>240                  245                  250 | 770 |
| tct gca aga aac tac att cag tct ctg gcc cag atg ccg aag atg aac<br>Ser Ala Arg Asn Tyr Ile Gln Ser Leu Ala Gln Met Pro Lys Met Asn<br>255                  260                  265 | 818 |
| ttc gca aat gta ttt att ggt gcc aat ccc ctg gct gtc gac ctg ctg<br>Phe Ala Asn Val Phe Ile Gly Ala Asn Pro Leu Ala Val Asp Leu Leu<br>270                  275                  280              285 | 866 |
| gaa aag atg ctg gtt ttg gac tcg gat aag agg atc aca gca gcc caa<br>Glu Lys Met Leu Val Leu Asp Ser Asp Lys Arg Ile Thr Ala Ala Gln<br>                290                  295                  300 | 914 |
| gct ctt gcg cat gcc tac ttt gct cag tac cac gac cct gat gat gag<br>Ala Leu Ala His Ala Tyr Phe Ala Gln Tyr His Asp Pro Asp Asp Glu<br>                305                  310                  315 | 962 |
| cca gtg gct gaa cct tat gac cag tcc ttt gaa agc agg gac ttc ctt<br>Pro Val Ala Glu Pro Tyr Asp Gln Ser Phe Glu Ser Arg Asp Phe Leu<br>                320                  325                  330 | 1010 |
| ata gac gaa tgg aag agc ctg acc tac gat gaa gtc att agc ttt gtg<br>Ile Asp Glu Trp Lys Ser Leu Thr Tyr Asp Glu Val Ile Ser Phe Val<br>335                  340                  345 | 1058 |
| cca ccg ccc ctt gac caa gaa gaa atg gag tcc tga gcaccttgct<br>Pro Pro Pro Leu Asp Gln Glu Glu Met Glu Ser<br>350                  355                  360 | 1104 |
| tctgttctgt ccatcccact tcactgtgag gggaaggcct gttcatggga actctccaaa | 1164 |
| taccattcaa gtgcctcttg ttgaaagatt ccttcatggt ggaaggggt gcatgtatgt | 1224 |
| gcgtagtgtt tgtgtgtgtc tgtctgtctg tccgtttgtc catgtatctt tgtggaagtc | 1284 |
| attgtgatgg cagtgacttc atgagtggta gatgctcctt ggcagtctgc ctgctctctc | 1344 |
| agagtccggg caggccgatg ggaactgccg tctccttagg gatgtgtgtg tgtatgttaa | 1404 |
| gtgcaaagta agaatattaa aatatccctg ttcctagtta ccttgccact tcggcttctc | 1464 |
| ctgtggccct gcctttacca tatcacagtg acagagagag gctgcttcag gtctgaggct | 1524 |
| atccctcagc catgcataaa gcccaagaga accaactggc tcctgggctc tagcctgtga | 1584 |
| tcggcttgct catgtcctca gaacctgtca gtctgtttgt gccttaaaag gagagaaggg | 1644 |
| cgcgttgtgg tagttacaga atctcagttg ctggcgttct gagccaggca aggcacaggg | 1704 |
| ctgttggatg gccagtgggg agctggacaa aacaaggcag ccttcaagga ggccatgggt | 1764 |
| gcatgtttgc atgagtgtat gtgcaaccgc cctccctcac ctccaggagc aagctgttt | 1824 |

-continued

| | |
|---|---:|
| ctatgcttac ctaagttcac ctcagtgcag aggtctccag tgccaggcac aggctcctgc | 1884 |
| catcagtagc ttcctatgtc atcttcacgt catgcgggtg tttgcatgct gtgctctgga | 1944 |
| gcttgtcctg tcttctggaa gccctgggcc gggcgtgtga agacttccca gcagtcctat | 2004 |
| ccacgcacct cagctgaggc cacgggcaca ctgctgcttc ctcactccag ctacgttgtg | 2064 |
| ttgaacacaa ctgatcctcc aggtgcttgt ggtgcaggaa acgggacgaa cagagcacct | 2124 |
| gaaccettgc catctgacat caccgacaca ggagaacagt cctctcctct cctctcctct | 2184 |
| cctctccctag gacagtcccc ggctctggaa tcatgttctt ctcactcatg gtagccagct | 2244 |
| aagaaagctg caaaccgaac aaagggagaa ccgagctcct gaagccagga gctcctttta | 2304 |
| ctgtccttct caaataggg tcattagaca cagccaagtc gtcaaaggcc ctttccttg | 2364 |
| tacggggccc ccccgccccc ggcagcttga cactgatttc agtgtctatt tggggagaaa | 2424 |
| gcaattttgt cttggaattt tgtatgttgt aggaatcctt agagagtgtg gttccttctg | 2484 |
| atggggagaa agggcaaatt attttaatat tttgtatttc acctttataa acatgaatcc | 2544 |
| tcagggtga agaacagttt gcataatttt ctgaatttca ggcactttgt gctatatgag | 2604 |
| gacccatata tttaagcttt ttgtgcagta agaaagtgta aagccaattc cagtgttgga | 2664 |
| cgaaacaggt ctcgtattta ggtcaaggtg tctccattct ctatcagtgc agggacatgc | 2724 |
| agtttctgtg gggcagggta ggaccctgca tcatttggag cccagaagga ggccgactgg | 2784 |
| ccaggcctca ccgcctcagt atgcagtcca gctccacgtc atcccctcac aatggttagt | 2844 |
| agcaacgtct gggtttgaac gccaggcgtg gttatattat tgaggatgcc tttgcacatg | 2904 |
| tggccatgct gtgttaggac tgtgccccag ggcccggact tgaagctaga gctggcagaa | 2964 |
| gagctcctgg catccatggt gcgatgctgc cgccacccag tttctccatt ggaagacaag | 3024 |
| ggaatgagaa gactgctgtg tatgtgtatt tgtgaacttg gttgtgatct ggtatgccat | 3084 |
| aggatgtcag acaatatcac tggttaaagt aaagcctatt tttcagat | 3132 |

<210> SEQ ID NO 46
<211> LENGTH: 360
<212> TYPE: PRT
<213> ORGANISM: Rattus norvegicus

<400> SEQUENCE: 46

Met Ser Gln Glu Arg Pro Thr Phe Tyr Arg Gln Leu Asn Lys Thr
1               5                   10                  15

Val Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly His
        35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

```
Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
    210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Ala Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
    290                 295                 300

His Ala Tyr Phe Ala Gln Tyr His Asp Pro Asp Glu Pro Val Ala
305                 310                 315                 320

Glu Pro Tyr Asp Gln Ser Phe Glu Ser Arg Asp Phe Leu Ile Asp Glu
                325                 330                 335

Trp Lys Ser Leu Thr Tyr Asp Glu Val Ile Ser Phe Val Pro Pro Pro
            340                 345                 350

Leu Asp Gln Glu Glu Met Glu Ser
        355                 360

<210> SEQ ID NO 47
<211> LENGTH: 20
<212> TYPE: DNA
<213> ORGANISM: Artificial Sequence
<220> FEATURE:
<223> OTHER INFORMATION: antisense sequence

<400> SEQUENCE: 47
ctgcgacatt ttccagcggc                                          20

<210> SEQ ID NO 48
<211> LENGTH: 20
<212> TYPE: DNA
<213> ORGANISM: Artificial Sequence
<220> FEATURE:
<223> OTHER INFORMATION: antisense sequence

<400> SEQUENCE: 48
ggtaagcttc tgacacttca                                          20

<210> SEQ ID NO 49
<211> LENGTH: 20
<212> TYPE: DNA
<213> ORGANISM: Artificial Sequence
<220> FEATURE:
<223> OTHER INFORMATION: antisense sequence

<400> SEQUENCE: 49
ggccagagac tgaatgtagt                                          20
```

```
<210> SEQ ID NO 50
<211> LENGTH: 20
<212> TYPE: DNA
<213> ORGANISM: Artificial Sequence
<220> FEATURE:
<223> OTHER INFORMATION: antisense sequence

<400> SEQUENCE: 50
catcatcagg gtcgtggtac                                              20

<210> SEQ ID NO 51
<211> LENGTH: 20
<212> TYPE: DNA
<213> ORGANISM: Artificial Sequence
<220> FEATURE:
<223> OTHER INFORMATION: antisense sequence

<400> SEQUENCE: 51
ggcacaaagc taatgacttc                                              20

<210> SEQ ID NO 52
<211> LENGTH: 20
<212> TYPE: DNA
<213> ORGANISM: Artificial Sequence
<220> FEATURE:
<223> OTHER INFORMATION: antisense sequence

<400> SEQUENCE: 52
aggtgctcag gactccattt                                              20

<210> SEQ ID NO 53
<211> LENGTH: 20
<212> TYPE: DNA
<213> ORGANISM: Artificial Sequence
<220> FEATURE:
<223> OTHER INFORMATION: antisense sequence

<400> SEQUENCE: 53
ggatggacag aacagaagca                                              20

<210> SEQ ID NO 54
<211> LENGTH: 20
<212> TYPE: DNA
<213> ORGANISM: Artificial Sequence
<220> FEATURE:
<223> OTHER INFORMATION: antisense sequence

<400> SEQUENCE: 54
gagcaggcag actgccaagg                                              20

<210> SEQ ID NO 55
<211> LENGTH: 20
<212> TYPE: DNA
<213> ORGANISM: Artificial Sequence
<220> FEATURE:
<223> OTHER INFORMATION: antisense sequence

<400> SEQUENCE: 55
aggctagagc ccaggagcca                                              20

<210> SEQ ID NO 56
<211> LENGTH: 20
<212> TYPE: DNA
<213> ORGANISM: Artificial Sequence
<220> FEATURE:
<223> OTHER INFORMATION: antisense sequence
```

```
<400> SEQUENCE: 56
gagcctgtgc ctggcactgg                                                     20

<210> SEQ ID NO 57
<211> LENGTH: 20
<212> TYPE: DNA
<213> ORGANISM: Artificial Sequence
<220> FEATURE:
<223> OTHER INFORMATION: antisense sequence

<400> SEQUENCE: 57
tgcaccacaa gcacctggag                                                     20

<210> SEQ ID NO 58
<211> LENGTH: 20
<212> TYPE: DNA
<213> ORGANISM: Artificial Sequence
<220> FEATURE:
<223> OTHER INFORMATION: antisense sequence

<400> SEQUENCE: 58
ggctaccatg agtgagaaga                                                     20

<210> SEQ ID NO 59
<211> LENGTH: 20
<212> TYPE: DNA
<213> ORGANISM: Artificial Sequence
<220> FEATURE:
<223> OTHER INFORMATION: antisense sequence

<400> SEQUENCE: 59
gtccctgcac tgatagagaa                                                     20

<210> SEQ ID NO 60
<211> LENGTH: 20
<212> TYPE: DNA
<213> ORGANISM: Artificial Sequence
<220> FEATURE:
<223> OTHER INFORMATION: antisense sequence

<400> SEQUENCE: 60
tcttccaatg gagaaactgg                                                     20

<210> SEQ ID NO 61
<211> LENGTH: 749
<212> TYPE: DNA
<213> ORGANISM: Mus musculus

<400> SEQUENCE: 61
tgctgggcgt ggggcgcggg ccgggtgctg cgcgcgggga tccggggcgc tcgctccagc         60
tgcttctgtg gatatgtcgg gtccgcgcgc gggattctac cggcaagagc tgaacaaaac        120
agtatgggag gtgccgcagc ggctgcaggg cctacgcccg gtgggctccg gcgcctacgg        180
ctcagtctgc tcggcctacg acgcgcggct gcgccagaag gtggcctgtaa agaagctgtc      240 tcgccctttc caatcgctga tccacgcgag gaggacatac cgtgagctgc gcctactcaa       300
gcacctgaag cacgagaacg tcataggact tttggacgtc ttcacgccgg ccacatccat       360
cgaggatttc agcgaagtgt acctcgtgac gaccctgatg ggcgccgacc tgaataacat       420
cgtcaagtgt caggccctga gcgatgagca tgttcaattc cttgtctacc agctgctgcg       480
tgggctgaag tatatccact cggcgggcat cattcaccgg gacctgaagc ccagcaatgt       540
agcggtgaac gaggactgcg agctgaggat cctggacttt gggctagcac gccaggctga       600
```

```
tgaggagatg accggatatg tggccacacg gtggtaccgg gcgccagaga tcatgctaaa      660
ctggatgcac tacaaccaga cagtggacat ctggtctgtg gcctgcttca tggcttgaac      720
tgctggaagg gaagggcctt ctttcctgg                                        749
```

<210> SEQ ID NO 62
<211> LENGTH:
<212> TYPE:
<213> ORGANISM:

<400> SEQUENCE: 62

This Sequence is intentionally skipped

<210> SEQ ID NO 63
<211> LENGTH: 20
<212> TYPE: DNA
<213> ORGANISM: Artificial Sequence
<220> FEATURE:
<223> OTHER INFORMATION: antisense sequence

<400> SEQUENCE: 63

```
cacagaagca gctggagcga                                                   20
```

<210> SEQ ID NO 64
<211> LENGTH: 20
<212> TYPE: DNA
<213> ORGANISM: Artificial Sequence
<220> FEATURE:
<223> OTHER INFORMATION: antisense sequence

<400> SEQUENCE: 64

```
tgcggcacct cccatactgt                                                   20
```

<210> SEQ ID NO 65
<211> LENGTH: 20
<212> TYPE: DNA
<213> ORGANISM: Artificial Sequence
<220> FEATURE:
<223> OTHER INFORMATION: antisense sequence

<400> SEQUENCE: 65

```
ccctgcagcc gctgcggcac                                                   20
```

<210> SEQ ID NO 66
<211> LENGTH: 20
<212> TYPE: DNA
<213> ORGANISM: Artificial Sequence
<220> FEATURE:
<223> OTHER INFORMATION: antisense sequence

<400> SEQUENCE: 66

```
gcagactgag ccgtaggcgc                                                   20
```

<210> SEQ ID NO 67
<211> LENGTH: 20
<212> TYPE: DNA
<213> ORGANISM: Artificial Sequence
<220> FEATURE:
<223> OTHER INFORMATION: antisense sequence

<400> SEQUENCE: 67

```
ttacagccac cttctggcgc                                                   20
```

```
<210> SEQ ID NO 68
<211> LENGTH: 20
<212> TYPE: DNA
<213> ORGANISM: Artificial Sequence
<220> FEATURE:
<223> OTHER INFORMATION: antisense sequence

<400> SEQUENCE: 68
gtatgtcctc ctcgcgtgga                                           20

<210> SEQ ID NO 69
<211> LENGTH: 20
<212> TYPE: DNA
<213> ORGANISM: Artificial Sequence
<220> FEATURE:
<223> OTHER INFORMATION: antisense sequence

<400> SEQUENCE: 69
atggatgtgg ccggcgtgaa                                           20

<210> SEQ ID NO 70
<211> LENGTH: 20
<212> TYPE: DNA
<213> ORGANISM: Artificial Sequence
<220> FEATURE:
<223> OTHER INFORMATION: antisense sequence

<400> SEQUENCE: 70
gaattgaaca tgctcatcgc                                           20

<210> SEQ ID NO 71
<211> LENGTH: 20
<212> TYPE: DNA
<213> ORGANISM: Artificial Sequence
<220> FEATURE:
<223> OTHER INFORMATION: antisense sequence

<400> SEQUENCE: 71
acattgctgg gcttcaggtc                                           20

<210> SEQ ID NO 72
<211> LENGTH: 20
<212> TYPE: DNA
<213> ORGANISM: Artificial Sequence
<220> FEATURE:
<223> OTHER INFORMATION: antisense sequence

<400> SEQUENCE: 72
atcctcagct cgcagtcctc                                           20

<210> SEQ ID NO 73
<211> LENGTH: 20
<212> TYPE: DNA
<213> ORGANISM: Artificial Sequence
<220> FEATURE:
<223> OTHER INFORMATION: antisense sequence

<400> SEQUENCE: 73
taccaccgtg tggccacata                                           20

<210> SEQ ID NO 74
<211> LENGTH: 20
<212> TYPE: DNA
<213> ORGANISM: Artificial Sequence
<220> FEATURE:
<223> OTHER INFORMATION: antisense sequence
```

```
<400> SEQUENCE: 74
cagtttagca tgatctctgg                                               20

<210> SEQ ID NO 75
<211> LENGTH: 20
<212> TYPE: DNA
<213> ORGANISM: Artificial Sequence
<220> FEATURE:
<223> OTHER INFORMATION: antisense sequence

<400> SEQUENCE: 75
caggccacag accagatgtc                                               20

<210> SEQ ID NO 76
<211> LENGTH: 20
<212> TYPE: DNA
<213> ORGANISM: Artificial Sequence
<220> FEATURE:
<223> OTHER INFORMATION: antisense sequence

<400> SEQUENCE: 76
ccttccagca gttcaagcca                                               20

<210> SEQ ID NO 77
<211> LENGTH: 20
<212> TYPE: DNA
<213> ORGANISM: Artificial Sequence
<220> FEATURE:
<223> OTHER INFORMATION: control sequence

<400> SEQUENCE: 77
cagcaccatg gacgcggaac                                               20

<210> SEQ ID NO 78
<211> LENGTH: 20
<212> TYPE: DNA
<213> ORGANISM: Artificial Sequence
<220> FEATURE:
<223> OTHER INFORMATION: antisense sequence

<400> SEQUENCE: 78
ctgagacatt ttccagcggc                                               20

<210> SEQ ID NO 79
<211> LENGTH: 20
<212> TYPE: DNA
<213> ORGANISM: Artificial Sequence
<220> FEATURE:
<223> OTHER INFORMATION: antisense sequence

<400> SEQUENCE: 79
acgctcgggc acctcccaga                                               20

<210> SEQ ID NO 80
<211> LENGTH: 20
<212> TYPE: DNA
<213> ORGANISM: Artificial Sequence
<220> FEATURE:
<223> OTHER INFORMATION: antisense sequence

<400> SEQUENCE: 80
agcttcttca ctgccacacg                                               20
```

```
<210> SEQ ID NO 81
<211> LENGTH: 20
<212> TYPE: DNA
<213> ORGANISM: Artificial Sequence
<220> FEATURE:
<223> OTHER INFORMATION: antisense sequence

<400> SEQUENCE: 81
aatgatggac tgaaatggtc                                                 20

<210> SEQ ID NO 82
<211> LENGTH: 20
<212> TYPE: DNA
<213> ORGANISM: Artificial Sequence
<220> FEATURE:
<223> OTHER INFORMATION: antisense sequence

<400> SEQUENCE: 82
tccaacagac caatcacatt                                                 20

<210> SEQ ID NO 83
<211> LENGTH: 20
<212> TYPE: DNA
<213> ORGANISM: Artificial Sequence
<220> FEATURE:
<223> OTHER INFORMATION: antisense sequence

<400> SEQUENCE: 83
tgtaagcttc tgacatttca                                                 20

<210> SEQ ID NO 84
<211> LENGTH: 20
<212> TYPE: DNA
<213> ORGANISM: Artificial Sequence
<220> FEATURE:
<223> OTHER INFORMATION: antisense sequence

<400> SEQUENCE: 84
tgaatgtata tactttagac                                                 20

<210> SEQ ID NO 85
<211> LENGTH: 20
<212> TYPE: DNA
<213> ORGANISM: Artificial Sequence
<220> FEATURE:
<223> OTHER INFORMATION: antisense sequence

<400> SEQUENCE: 85
ctcacagtct tcattcacag                                                 20

<210> SEQ ID NO 86
<211> LENGTH: 20
<212> TYPE: DNA
<213> ORGANISM: Artificial Sequence
<220> FEATURE:
<223> OTHER INFORMATION: antisense sequence

<400> SEQUENCE: 86
cacgtagcct gtcatttcat                                                 20

<210> SEQ ID NO 87
<211> LENGTH: 20
<212> TYPE: DNA
<213> ORGANISM: Artificial Sequence
<220> FEATURE:
<223> OTHER INFORMATION: antisense sequence
```

-continued

```
<400> SEQUENCE: 87
catcccactg accaaatatc                                                    20

<210> SEQ ID NO 88
<211> LENGTH: 20
<212> TYPE: DNA
<213> ORGANISM: Artificial Sequence
<220> FEATURE:
<223> OTHER INFORMATION: antisense sequence

<400> SEQUENCE: 88
tatggtctgt accaggaaac                                                    20

<210> SEQ ID NO 89
<211> LENGTH: 20
<212> TYPE: DNA
<213> ORGANISM: Artificial Sequence
<220> FEATURE:
<223> OTHER INFORMATION: antisense sequence

<400> SEQUENCE: 89
agtcaaagac tgaatatagt                                                    20

<210> SEQ ID NO 90
<211> LENGTH: 20
<212> TYPE: DNA
<213> ORGANISM: Artificial Sequence
<220> FEATURE:
<223> OTHER INFORMATION: antisense sequence

<400> SEQUENCE: 90
ttctcttatc tgagtccaat                                                    20

<210> SEQ ID NO 91
<211> LENGTH: 20
<212> TYPE: DNA
<213> ORGANISM: Artificial Sequence
<220> FEATURE:
<223> OTHER INFORMATION: antisense sequence

<400> SEQUENCE: 91
catcatcagg atcgtggtac                                                    20

<210> SEQ ID NO 92
<211> LENGTH: 20
<212> TYPE: DNA
<213> ORGANISM: Artificial Sequence
<220> FEATURE:
<223> OTHER INFORMATION: antisense sequence

<400> SEQUENCE: 92
tcaaaggact gatcataagg                                                    20

<210> SEQ ID NO 93
<211> LENGTH: 20
<212> TYPE: DNA
<213> ORGANISM: Artificial Sequence
<220> FEATURE:
<223> OTHER INFORMATION: antisense sequence

<400> SEQUENCE: 93
ggcacaaagc tgatgacttc                                                    20
```

-continued

```
<210> SEQ ID NO 94
<211> LENGTH: 20
<212> TYPE: DNA
<213> ORGANISM: Artificial Sequence
<220> FEATURE:
<223> OTHER INFORMATION: antisense sequence

<400> SEQUENCE: 94
aggtgctcag gactccatct                                              20

<210> SEQ ID NO 95
<211> LENGTH: 20
<212> TYPE: DNA
<213> ORGANISM: Artificial Sequence
<220> FEATURE:
<223> OTHER INFORMATION: antisense sequence

<400> SEQUENCE: 95
gcaacaagag gcacttgaat                                              20
```

ANTISENSE MODULATION OF P38 MITOGEN ACTIVATED PROTEIN KINASE EXPRESSION

FIELD OF THE INVENTION

This invention relates to compositions and methods for modulating expression of p38 mitogen activated protein kinase genes, a family of naturally present cellular genes involved in signal transduction, and inflammatory and apoptotic responses. This invention is also directed to methods for inhibiting inflammation or apoptosis; these methods can be used diagnostically or therapeutically. Furthermore, this invention is directed to treatment of diseases or conditions associated with expression of p38 mitogen activated protein kinase genes.

BACKGROUND OF THE INVENTION

Cellular responses to external factors, such as growth factors, cytokines, and stress conditions, result in altered gene expression. These signals are transmitted from the cell surface to the nucleus by signal transduction pathways. Beginning with an external factor binding to an appropriate receptor, a cascade of signal transduction events is initiated. These responses are mediated through activation of various enzymes and the subsequent activation of specific transcription factors. These activated transcription factors then modulate the expression of specific genes.

The phosphorylation of enzymes plays a key role in the transduction of extracellular signals into the cell. Mitogen activated protein kinases (MAPKs), enzymes which effect such phosphorylations are targets for the action of growth factors, hormones, and other agents involved in cellular metabolism, proliferation and differentiation (Cobb et al., *J. Biol. Chem.*, 1995, 270, 14843). Mitogen activated protein kinases were initially discovered due to their ability to be tyrosine phosphorylated in response to exposure to bacterial lipopolysaccharides or hyperosmotic conditions (Han et al, *Science*, 1994, 265, 808). These conditions activate inflammatory and apoptotic responses mediated by MAPK. In general, MAP kinases are involved in a variety of signal transduction pathways (sometimes overlapping and sometimes parallel) that function to convey extracellular stimuli to protooncogene products to modulate cellular proliferation and/or differentiation (Seger et al., *FASEB J.*, 1995, 9, 726; Cano et al., *Trends Biochem. Sci.*, 1995, 20, 117).

One of the MAPK signal transduction pathways involves the MAP kinases p38α and p38β (also known as CSaids Binding Proteins, CSBP). These MAP kinases are responsible for the phosphorylation of ATF-2, MEFC2 and a variety of other cellular effectors that may serve as substrates for p38 MAPK proteins (Kummer et al, *J. Biol. Chem.*, 1997, 272, 20490).

Phosphorylation of p38 MAPKs potentiates the ability of these factors to activate transcription (Raingeaud et al, *Mol. Cell, Bio.*, 1996, 16, 1247; Han et al, *Nature*, 1997, 386, 296). Among the genes activated by the p38 MAPK signaling pathway is IL-6 (De Cesaris, P., et al., *J. Biol. Chem.*, 1998, 273, 7566–7571).

Besides p38α and p38β, other p38 MAPK family members have been described, including p38γ (Li et al, *Biochem. Biophys. Res. Commun.*, 1996, 228, 334), and p38δ (Jiang et al, *J. Biol. Chem.*, 1997, 272, 30122). The term "p38" as used herein shall mean a member of the p38 MAPK family, including but not limited to p38α, p38β, p38γ and p38δ, their isoforms (Kumar et al, *Biochem. Biophys. Res. Commun.*, 1997, 235, 533) and other members of the p38 MAPK family of proteins whether they function as p38 MAP kinases per se or not.

Modulation of the expression of one or more p38 MAPKs is desirable in order to interfere with inflammatory or apoptotic responses associated with disease states and to modulate the transcription of genes stimulated by ATF-2, MEFC2 and other p38 MAPK phosphorylation substrates.

Inhibitors of p38 MAPKs have been shown to have efficacy in animal models of arthritis (Badger, A. M., et al., *J. Pharmacol. Exp. Ther.*, 1996, 279, 1453–1461) and angiogenesis (Jackson, J. R., et al., *J. Pharmacol. Exp. Ther.*, 1998, 284, 687–692). MacKay, K. and Mochy-Rosen, D. (*J. Biol. Chem.*, 1999, 274, 6272–6279) demonstrate that an inhibitor of p38 MAPKs prevents apoptosis during ischemia in cardiac myocytes, suggesting that p38 MAPK inhibitors can be used for treating ischemic heart disease. p38 MAPK also is required for T-cell HIV-1 replication (Cohen et al, *Mol. Med.*, 1997, 3, 339) and may be a useful target for AIDS therapy. Other diseases believed to be amenable to treatment by inhibitors of p38 MAPKs are disclosed in U.S. Pat. No. 5,559,137, herein incorporated by reference.

Therapeutic agents designed to target p38 MAPKs include small molecule inhibitors and antisense oligonucleotides. Small molecule inhibitors based on pyridinyl imidazole are described in U.S. Pat. Nos. 5,670,527; 5,658,903; 5,656,644; 5,559,137; 5,593,992; and 5,593,991. WO 98/27098 and WO 99/00357 describe additional small molecule inhibitors, one of which has entered clinical trials. Other small molecule inhibitors are also known.

Antisense therapy represents a potentially more specific therapy for targeting p38 MAPKs and, in particular, specific p38 MAPK isoforms. Nagata, Y., et al. (*Blood*, 1998, 6, 1859–1869) disclose an antisense phosphothioester oligonucleotide targeted to the translational start site of mouse p38b (p38β). Aoshiba, K., et al. (*J. Immunol.*, 1999, 162, 1692–1700) and Cohen, P. S., et al. (*Mol. Med.*, 1997, 3, 339–346) disclose a phosphorothioate antisense oligonucleotide targeted to the coding regions of human p38α, human p38β and rat p38.

There remains a long-felt need for improved compositions and methods for modulating the expression of p38 MAP kinases.

SUMMARY OF THE INVENTION

The present invention provides antisense compounds which are targeted to nucleic acids encoding a p38 MAPK and are capable of modulating p38 MAPK expression. The present invention also provides oligonucleotides targeted to nucleic acids encoding a p38 MAPK. The present invention also comprises methods of modulating the expression of a p38 MAPK, in cells and tissues, using the oligonucleotides of the invention. Methods of inhibiting p38 MAPK expression are provided; these methods are believed to be useful both therapeutically and diagnostically. These methods are also useful as tools, for example, for detecting and determining the role of p38 MAPKs in various cell functions and physiological processes and conditions and for diagnosing conditions associated with expression of p38 MAPKs.

The present invention also comprises methods for diagnosing and treating inflammatory diseases, particularly rheumatoid arthritis. These methods are believed to be useful, for example, in diagnosing p38 MAPK-associated disease progression. These methods employ the oligonucleotides of the invention. These methods are believed to be useful both therapeutically, including prophylactically, and as clinical research and diagnostic tools.

DETAILED DESCRIPTION OF THE INVENTION p38 MAPKs play an important role in signal transduction in response to cytokines, growth factors and other cellular stimuli. Specific responses elicited by p38 include inflammatory and apoptotic responses. Modulation of p38 may be useful in the treatment of inflammatory diseases, such as rheumatoid arthritis.

The present invention employs antisense compounds, particularly oligonucleotides, for use in modulating the function of nucleic acid molecules encoding a p38 MAPK, ultimately modulating the amount of a p38 MAPK produced. This is accomplished by providing oligonucleotides which specifically hybridize with nucleic acids, preferably mRNA, encoding a p38 MAPK.

The antisense compounds may be used to modulate the function of a particular p38 MAPK isoform, e.g. for research purposes to determine the role of a particular isoform in a normal or disease process, or to treat a disease or condition that may be associated with a particular isoform. It may also be desirable to target multiple p38 MAPK isoforms. In each case, antisense compounds can be designed by taking advantage of sequence homology between the various isoforms. If an antisense compound to a particular isoform is desired, then the antisense compound is designed to a unique region in the desired isoform's gene sequence. With such a compound, it is desirable that this compound does not inhibit the expression of other isoforms. Less desirable, but acceptable, are compounds that do not substantially inhibit other isoforms. By "substantially", it is intended that these compounds do not inhibit the expression of other isoforms greater than 25%; more preferred are compounds that do not inhibit other isoforms greater than 10%. If an antisense compound is desired to target multiple p38 isoforms, then regions of significant homology between the isoforms can be used.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding a p38 MAPK; in other words, a p38 MAPK gene or RNA expressed from a p38 MAPK gene. p38 MAPK mRNA is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding p38, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5°-TAA, 5°-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene) and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene). mRNA splice sites may also be preferred target regions, and are particularly useful in situations where aberrant splicing is implicated in disease, or where an overproduction of a particular mRNA splice product is implicated in disease. Aberrant fusion junctions due to rearrangements or deletions may also be preferred targets.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand.

Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment and, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA.

The overall effect of interference with mRNA function is modulation of p38 MAPK expression. In the context of this invention "modulation" means either inhibition or stimulation; i.e., either a decrease or increase in expression. This modulation can be measured in ways which are routine in the art, for example by Northern blot assay of mRNA expression as taught in the examples of the instant application or by Western blot or ELISA assay of protein expression, or by an immunoprecipitation assay of protein expression, as taught in the examples of the instant application. Effects on cell proliferation or tumor cell growth can also be measured, as taught in the examples of the instant application.

The oligonucleotides of this invention can be used in diagnostics, therapeutics, prophylaxis, and as research reagents and in kits. Since the oligonucleotides of this invention hybridize to nucleic acids encoding a p38 MAPK, sandwich, calorimetric and other assays can easily be constructed to exploit this fact. Furthermore, since the oligonucleotides of this invention hybridize specifically to nucleic acids encoding particular isoforms of p38 MAPK, such assays can be devised for screening of cells and tissues for particular p38 MAPK isoforms. Such assays can be utilized for diagnosis of diseases associated with various p38 MAPK isoforms. Provision of means for detecting hybridization of oligonucleotide with a p38 MAPK gene or mRNA can routinely be accomplished. Such provision may include enzyme conjugation, radiolabelling or any other suitable detection systems. Kits for detecting the presence or absence of p38 MAPK may also be prepared.

The present invention is also suitable for diagnosing abnormal inflammatory states in tissue or other samples from patients suspected of having an inflammatory disease such as rheumatoid arthritis. The ability of the oligonucleotides of the present invention to inhibit inflammation may be employed to diagnose such states. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal. Similarly, the present invention can be used to distinguish p38 MAPK-associated diseases, from diseases having other etiologies, in order that an efficacious treatment regime can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). Preferred embodiments comprise at least an 815 nucleobase portion of a sequence of an antisense compound which inhibits the expression of a p38 mitogen activated kinase. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates (usually abbreviated in the art as P=S) and those with $CH_2$—NH—O—$CH_2$, $CH_2$—N ($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester (usually abbreviated in the art as P=O) backbone is represented as O—P—O—$CH_2$). Also preferred are oligonucleotides having morpholino backbone structures (Summerton and Weller, U.S. Pat. No. 5,034,506). Further preferred are oligonucleotides with NR—C(*)—CH$_2$—CH$_2$, CH$_2$—NR—C(*)—CH$_2$, CH$_2$—CH$_2$—NR—C(*), C(*)—NR—CH$_2$—CH$_2$ and CH$_2$—C(*)—NR—CH$_2$ backbones, wherein "*" represents O or S (known as amide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science,* 1991, 254, 1497; U.S. Pat. No. 5,539,082). Other preferred modified oligonucleotides may contain one or more substituted sugar moieties comprising one of the following at the 2' position: OH, SH, SCH$_3$, F, OCN, OCH$_3$OCH$_3$, OCH$_3$O(CH$_2$)$_n$CH$_3$, O(CH$_2$)$_n$NH$_2$ or O(CH$_2$)$_n$CH$_3$ where n is from 1 to about 10; C$_1$ to C$_{10}$ lower alkyl, alkoxyalkoxy, substituted lower alkyl, alkaryl or aralkyl; Cl; Br; CN; CF$_3$; OCF$_3$; O-, S-, or N-alkyl; O-, S-, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-O-methoxyethyl [which can be written as 2'-O—CH$_2$CH$_2$OCH$_3$, and is also known in the art as 2'-O—(2-methoxyethyl) or 2'-methoxyethoxy] [Martin et al., *Helv. Chim. Acta,* 1995, 78, 486]. Other preferred modifications include 2'-methoxy (2'-OCH$_3$), 2'-propoxy (2'-OCH$_2$CH$_2$CH$_3$), 2'-aminopropoxy (2'-OCH$_2$CH$_2$CH$_2$NH$_2$) and 2'-fluoro (2'-F). Further preferred modifications include 2'-dimethylaminooxyethoxy, i.e., a O(CH$_2$)$_2$ON(CH$_3$)$_2$ group, also known as 2'-DMAOE, and 2'-dimethylaminoethoxyethoxy (2'-DMAEOE), i.e. 2'-O—CH$_2$—O—CH$_2$N(CH$_2$)$_2$. Similar modifications may also be made at other positions on the oligonucleotide, particularly the 3' position of the sugar on the 3' terminal nucleotide and the 5' position of the 5' terminal nucleotide. Oligonucleotides may also have sugar mimetics such as cyclobutyls in place of the pentofuranosyl group.

The oligonucleotides of the invention may additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine and 5-methylcytosine, as well as synthetic nucleobases, e.g., 5-bromouracil, 5-hydroxymethyluracil, 8-azaguanine, 7-deazaguanine, N$^6$(6-aminohexyl)adenine and 2,6-diaminopurine [Kornberg, A., DNA Replication, 1974, W.H. Freeman & Co., San Francisco, 1974, pp. 75–77; Gebeyehu, G., et al., *Nucleic Acids Res.,* 1987, 15, 4513]. 5-methylcytosine (5-me-C) is presently a preferred nucleobase, particularly in combination with 2'-O-methoxyethyl modifications.

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The N$^6$ position of a purine nucleobase may also be utilized to link a lipophilic moiety to an oligonucleotide of the invention (Gebeyehu, G., et al., *Nucleic Acids Res.,* 1987, 15, 4513). Such lipophilic moieties include but are not limited to a cholesteryl moiety [Letsinger et al., *Proc. Natl. Acad. Sci. USA,* 1989, 86, 6553], cholic acid [Manoharan et al., *Bioorg. Med. Chem. Let.,* 1994, 4, 1053], a thioether, e.g., hexyl-S-tritylthiol [Manoharan et al., *Ann. N.Y. Acad. Sci.,* 1992, 660, 306; Manoharan et al., *Bioorg. Med. Chem. Let.,* 1993, 3, 2765], a thiocholesterol [Oberhauser et al., *Nucl. Acids Res.,* 1992, 20, 533], an aliphatic chain, e.g., dodecandiol or undecyl residues [Saison-Behmoaras et al., *EMBO J.,* 1991, 10, 111; Kabanov et al., *FEBS Lett.,* 1990, 259, 327; Svinarchuk et al., *Biochimie.,* 1993, 75, 49], a phospholipid, e.g., di-hexadecyl-rac-glycerol or triethylammonium 1,2-di-O-hexadecyl-racglycero-3-H-phosphonate [Manoharan et al., *Tetrahedron Lett.,* 1995, 36, 3651; Shea et al., *Nucl. Acids Res.,* 1990, 18, 3777], a polyamine or a polyethylene glycol chain [Manoharan et al., *Nucleosides & Nucleotides,* 1995, 14, 969], or adamantane acetic acid [Manoharan et al., *Tetrahedron Lett.,* 1995, 36, 3651], a palmityl moiety [Mishra et al., *Biochim. Biophys. Acta,* 1995, 1264, 229], or an octadecylamine or hexylamino-carbonyl-oxycholesterol moiety [Crooke et al., *J. Pharmacol. Exp. Ther.,* 1996, 277, 923]. Oligonucleotides comprising lipophilic moieties, and methods for preparing such oligonucleotides, as disclosed in U.S. Pat. No. 5,138,045, U.S. Pat. No. 5,218,105 and U.S. Pat. No. 5,459,255, the contents of which are hereby incorporated by reference.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., 2'-fluoro- or 2'-O-methoxyethyl-substituted). Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—CH$_2$CH$_2$OCH$_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—CH$_2$CH$_2$OCH$_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred. Through use of such modifications, active oligonucleotides have been identified which are shorter than conventional "first generation" oligonucleotides active against p38. Oligonucleotides in accordance with this invention are from 5 to 50 nucleotides in length. In the context of this invention it is understood that this encompasses non-naturally occurring oligomers as hereinbefore described, having from 5 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides [Martin, P., *Helv. Chim. Acta*, 1995, 78, 486]. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids.

Pharmaceutically acceptable "salts" are physiologically and pharmaceutically acceptable salts of the nucleic acids of the invention: i.e., salts that retain the desired biological activity of the parent compound and do not impart undesired toxicological effects thereto [see, for example, Berge et al., "Pharmaceutical Salts," *J. of Pharma Sci.*, 1977, 66, 1].

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems*, 1991, 8:91–192; Muranishi, *Critical Reviews in Therapeutic Drug Carrier Systems*, 1990, 7:1). One or more penetration enhancers from one or more of these broad categories may be included.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure.

A preferred colloidal dispersion system is a plurality of liposomes. Liposomes are microscopic spheres having an aqueous core surrounded by one or more outer layers made up of lipids arranged in a bilayer configuration [see, generally, Chonn et al., Current Op. Biotech., 1995, 6, 698].

The pharmaceutical compositions of the present invention may be administered in a number of ways depending upon whether local or systemic treatment is desired and upon the area to be treated. Administration may be topical (including ophthalmic, vaginal, rectal, intranasal, epidermal and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bischloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, The Merck Manual of Diagnosis and Therapy, 15th Ed., pp. 1206–1228, Berkow et al., eds., Rahay, N.J., 1987). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

Thus, in the context of this invention, by "therapeutically effective amount" is meant the amount of the compound which is required to have a therapeutic effect on the treated mammal. This amount, which will be apparent to the skilled artisan, will depend upon the type of mammal, the age and weight of the mammal, the type of disease to be treated, perhaps even the gender of the mammal, and other factors which are routinely taken into consideration when treating a mammal with a disease. A therapeutic effect is assessed in the mammal by measuring the effect of the compound on the disease state in the animal. For example, if the disease to be treated is cancer, therapeutic effects are assessed by measuring the rate of growth or the size of the tumor, or by measuring the production of compounds such as cytokines, production of which is an indication of the progress or regression of the tumor.

The following examples illustrate the present invention and are not intended to limit the same.

EXAMPLES

Example 1: Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step.

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides are synthesized as described in Kawasaki et al., *J. Med. Chem.*, 1993, 36, 831. Briefly, the protected nucleoside N$^6$-benzoyl-2'-deoxy-2'-fluoroadenosine is synthesized utilizing commercially available 9-β-D-arabinofuranosyladenine as starting material and by modifying literature procedures whereby the 2'-α-fluoro atom is introduced by a S$_N$2-displacement of a 2'-α-O-trifyl group. Thus N$^6$-benzoyl-9-β-D-arabinofuranosyladenine is selectively protected in moderate yield as the 3',5'-ditetrahydropyranyl (THP) intermediate. Deprotection of the THP and N$^6$-benzoyl groups is accomplished using standard methodologies and standard methods are used to obtain the 5'-dimethoxytrityl-(DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and conversion to the intermediate diisobutyrylarabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2,2'-anhydro-1-β-D-arabinofuranosyluracil is treated with 70% hydrogen fluoride-pyridine. Standard procedures are used to obtain the 5'-DMT and 5'-DMT-3'phosphoramidites.

2'-deoxy-2'-fluorocytidine is synthesized via amination of 2'-deoxy-2'-fluorouridine, followed by selective protection to give N$^4$-benzoyl-2'-deoxy-2'-fluorocytidine. Standard procedures are used to obtain the 5'-DMT and 5'-DMT-3'-phosphoramidites.

2'-(2-methoxyethyl)-modified amidites were synthesized according to Martin, P., *Helv. Chim. Acta*, 1995, 78, 486. For ease of synthesis, the last nucleotide was a deoxynucleotide. 2'-O—CH$_2$CH$_2$OCH$_3$-cytosines may be 5-methyl cytosines.

5-Methyl cytosine monomers:

2,2'-Anhydro[1-(β-D-arabinofuranosyl)-5-methyluridine]:

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 hours) to give a solid which was crushed to a light tan powder (57 g, 85% crude yield). The material was used as is for further reactions.

2'-O-Methoxyethyl-5-methyluridine:

2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in CH$_3$CN (600 mL) and evaporated. A silica gel column (3 kg) was packed in CH$_2$Cl$_2$/acetone/MeOH (20:5:3) containing 0.5% Et$_3$NH. The residue was dissolved in CH$_2$Cl$_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxyrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with CH$_3$CN (200 mL). The residue was dissolved in CHCl$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/Hexane/Acetone (5:5:1) containing 0.5% Et$_3$NH. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine:

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 L of CHCl$_3$. The combined organics were dried with sodium sulfate and evaporated to give 122 g of residue (approx. 90% product). The residue was purified on a 3.5 kg silica gel column and eluted using EtOAc/Hexane (4:1). Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methylcytidine:

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite:

N$^4$-Benzoyl-2'-O-methoxyethyl-5'-O-dimethoxytrityl-5-methylcytidine (74 g, 0.10 M) was dissolved in CH$_2$Cl$_2$ (1 L) Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligo-nucleotides were synthesized according to published methods [Sanghvi et al., *Nucl. Acids Res.*, 1993, 21, 3197] using commercially available phosphoramidites (Glen Research, Sterling Va. or ChemGenes, Needham Mass.).

2'-O-(dimethylaminooxyethyl) nucleoside amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine:

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) are dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) is added in one portion. The reaction is stirred for 16 h at ambient temperature. TLC (Rf 0.22, ethyl acetate) indicates a complete reaction. The solution is concentrated under reduced pressure to a thick oil. This is partitioned between dichloromethane (1 L) and saturated sodium bicarbonate (2×1 L) and brine (1 L). The organic layer is dried over sodium sulfate and concentrated under reduced pressure to a thick oil. The oil is dissolved in a 1:1 mixture of ethyl acetate and ethyl ether (600 mL) and the solution is cooled to −10° C. The resulting crystalline product is collected by filtration, washed with ethyl ether (3×200 mL) and dried (40° C., 1 mm Hg, 24 h) to 149 g (74.8%) of white solid. TLC and NMR are used to check consistency with pure product.

5'-O-tert-Butyldiphenylsilyl-2'-O-(2-hydroxyethyl)-5-methyluridine:

In a 2 L stainless steel, unstirred pressure reactor is added borane in tetrahydrofuran (1.0 M, 2.0 eq, 622 mL). In the fume hood and with manual stirring, ethylene glycol (350 mL, excess) is added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) are added with manual stirring. The reactor is sealed and heated in an oil bath until an internal temperature of 160° C. is reached and then maintained for 16 h (pressure<100 psig). The reaction vessel is cooled to ambient and opened. TLC (Rf 0.67 for desired product and Rf 0.82 for ara-T side product, ethyl acetate) indicates % conversion to the product. In order to avoid additional side product formation, the reaction is stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue is purified by column chromatography (2 kg silica gel, ethyl acetate-hexanes gradient 1:1 to 4:1). The appropriate fractions are combined, stripped and dried to product as a white crisp foam (84 g, 50%), contaminated starting material (17.4 g) and pure reusable starting material 20 g. TLC and NMR are used to determine consistency with pure product.

2'-O-([2-phthalimidoxy)ethyl]-5'-t-butyldiphenylsilyl-5-methyluridine:

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethylazodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819, 86%).

5'-O-tert-butyldiphenylsilyl-2'-O-[(2-formadoximinooxy) ethyl]-5-methyluridine:

2'-O-([2-phthalimidoxy)ethyl]-5'-t-butyldiphenylsilyl-5-methyluridine (3.1 g, 4.5 mmol) is dissolved in dry $CH_2Cl_2$ (4.5 mL) and methylhydrazine (300 mL, 4.64 mmol) is added dropwise at −10° C. to 0° C. After 1 hr the mixture is filtered, the filtrate is washed with ice cold $CH_2Cl_2$ and the combined organic phase is washed with water, brine and dried over anhydrous $Na_2SO_4$. The solution is concentrated to get 2'-O-(aminooxyethyl) thymidine, which is then dissolved in MeOH (67.5 mL). To this formaldehyde (20% aqueous solution, w/w, 1.1 eg.) is added and the mixture for 1 hr. Solvent is removed under vacuum; residue chromatographed to get 5'-O-tert-butyldiphenylsilyl-2'-O-[(2-formadoximinooxy) ethyl]-5-methyluridine as white foam.

5'-O-tert-Butyldiphenylsilyl-2'-O-[N,N-dimethylaminooxyethyl]-5-methyluridine:

5'-O-tert-butyldiphenylsilyl-2'-O-[(2-formadoximinooxy) ethyl]-5-methyluridine (1.77 g, 3.12 mmol) is dissolved in a solution of 1M pyridinium p-toluenesulfonate (PPTS) in dry MeOH (30.6 mL). Sodium cyanoborohydride (0.39 g, 6.13 mmol) is added to this solution at 10° C. under inert atmosphere. The reaction mixture is stirred for 10 minutes at 10° C. After that the reaction vessel is removed from the ice bath and stirred at room temperature for 2 hr, the reaction monitored by TLC (5% MeOH in $CH_2Cl_2$). Aqueous $NaHCO_3$ solution (5%, 10 mL) is added and extracted with ethyl acetate (2×20 mL). Ethyl acetate phase is dried over anhydrous $Na_2SO_4$, evaporated to dryness. Residue is dissolved in a solution of 1M PPTS in MeOH (30.6 mL). Formaldehyde (20% w/w, 30 mL, 3.37 mmol) is added and the reaction mixture is stirred at room temperature for 10 minutes. Reaction mixture cooled to 10° C. in an ice bath, sodium cyanoborohydride (0.39 g, 6.13 mmol) is added and reaction mixture stirred at 10° C. for 10 minutes. After 10 minutes, the reaction mixture is removed from the ice bath and stirred at room temperature for 2 hrs. To the reaction mixture 5% $NaHCO_3$ (25 mL) solution is added and extracted with ethyl acetate (2×25 mL). Ethyl acetate layer is dried over anhydrous $Na_2SO_4$ and evaporated to dryness. The residue obtained is purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g).

2'-O-(dimethylaminooxyethyl)-5-methyluridine:

Triethylamine trihydrofluoride (3.91 mL, 24.0 mmol) is dissolved in dry THF and triethylamine (1.67 mL, 12 mmol, dry, kept over KOH). This mixture of triethylamine-2HF is then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction is monitored by TLC (5% MeOH in $CH_2Cl_2$). Solvent is removed under vacuum and the residue placed on a flash column and eluted with 10% MeOH in $CH_2Cl_2$ to get 2'-O-(dimethylaminooxyethyl)-5-methyluridine (766 mg).

5'-O-DMT-2'-O-(dimethylaminooxyethyl)-5-methyluridine:

2'-O-(dimethylaminooxyethyl)-5-methyluridine (750 mg, 2.17 mmol) is dried over $P_2O_5$ under high vacuum overnight at 40° C. It is then co-evaporated with anhydrous pyridine (20 mL). The residue obtained is dissolved in pyridine (11 mL) under argon atmosphere. 4-dimethylaminopyridine (26.5 mg, 2.60 mmol), 4,4'-dimethoxytrityl chloride (880 mg, 2.60 mmol) is added to the mixture and the reaction mixture is stirred at room temperature until all of the starting material disappeared. Pyridine is removed under vacuum and the residue chromatographed and eluted with 10% MeOH in $CH_2Cl_2$ (containing a few drops of pyridine) to get 5'-O-DMT-2'-O-(dimethylaminooxyethyl)-5-methyluridine (1.13 g).

5'-O-DMT-2'-O-(2-N,N-dimethylaminooxyethyl)-5-methyluridine-3'-[(2-cyanoethyl)-N,N-diisopropylphosphoramidite]:

5'-O-DMT-2'-O-(dimethylaminooxyethyl)-5-methyluridine (1.08 g, 1.67 mmol) is co-evaporated with toluene (20 mL). To the residue N,N-diisopropylamine tetrazonide (0.29 g, 1.67 mmol) is added and dried over $P_2O_5$ under high vacuum overnight at 40° C. Then the reaction mixture is dissolved in anhydrous acetonitrile (8.4 mL) and 2-cyanoethyl-N,N,N$^1$,N$^1$-tetraisopropylphosphoramidite (2.12 mL, 6.08 mmol) is added. The reaction mixture is stirred at ambient temperature for 4 hrs under inert atmosphere. The progress of the reaction was monitored by TLC (hexane:ethyl acetate 1:1). The solvent is evaporated, then the residue is dissolved in ethyl acetate (70 mL) and washed with 5% aqueous $NaHCO_3$ (40 mL). Ethyl acetate layer is dried over anhydrous $Na_2SO_4$ and concentrated. Residue obtained is chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]:

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxy trityl)guanosine which may be reduced to provide 2-N-isobutyryl-6-O-diphenylcarbamoyl-2'-O-(2-ethylacetyl) 5'-O-(4,4'-dimethoxytrityl) guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

Oligonucleotides having methylene(methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages were synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al., *Acc. Chem. Res.,* 1995, 28, 366. The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al., *Science,* 1991, 254, 1497.

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.,* 1991, 266, 18162. Results obtained with HPLC-purified material were similar to those obtained with non-HPLC purified material.

Example 2: Human p38α Oligonucleotide Sequences

Antisense oligonucleotides were designed to target human p38α. Target sequence data are from the p38 MAPK cDNA sequence; Genbank accession number L35253, provided herein as SEQ ID NO: 1. Oligonucleotides was synthesized as chimeric oligonucleotides ("gapmers") 20 nucleotides in length, composed of a central "gap" region consisting of eight 2'-deoxynucleotides, which is flanked on both sides (5' and 3' directions) by six-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines were 5-methyl-cytosines. These oligonucleotide sequences are shown in Table 1.

The human Jurkat T-cell line (American Type Culture Collection, Manassas, Va.) was maintained in RPMI 1640 growth media supplemented with 10% fetal bovine serum (FBS; Hyclone, Logan, Utah). HUVEC cells (Clonetics, San Diego, Calif.) were cultivated in endothelial basal media supplemented with 10% FBS (Hyclone, Logan, Utah).

Jurkat cells were grown to approximately 75% confluency and resuspended in culture media at a density of 1×10$^7$ cells/ml. A total of 3.6×10$^6$ cells were employed for each treatment by combining 360 μl of cell suspension with oligonucleotide at the indicated concentrations to reach a final volume of 400 μl. Cells were then transferred to an electroporation cuvette and electroporated using an Electrocell Manipulator 600 instrument (Biotechnologies and Experimental Research, Inc.) employing 150 V, 1000 μF, at 13Ω. Electroporated cells were then transferred to conical tubes containing 5 ml of culture media, mixed by inversion, and plated onto 10 cm culture dishes.

HUVEC cells were allowed to reach 75% confluency prior to use. The cells were washed twice with warm (37° C.) OPTI-MEM™ (Life Technologies). The cells were incubated in the presence of the appropriate culture medium, without the growth factors added, and the oligonucleotide formulated in LIPOFECTIN® (Life Technologies), a 1:1 (w/w) liposome formulation of the cationic lipid N-[1-(2,3-dioleyloxy)propyl]-n,n,n-trimethylammonium chloride (DOTMA), and dioleoyl phosphotidylethanolamine (DOPE) in membrane filtered water. HUVEC cells were treated with 100 nM oligonucleotide in 10 μg/ml LIPOFECTIN®. Treatment was for four hours.

Total mRNA was isolated using the RNEASY® Mini Kit (Qiagen, Valencia, Calif.; similar kits from other manufacturers may also be used), separated on a 1% agarose gel, transferred to HYBOND™-N+ membrane (Amersham Pharmacia Biotech, Piscataway, N.J.), a positively charged nylon membrane, and probed. p38 MAPK probes were made using the Prime-A-Gene® kit (Promega Corporation, Madison, Wis.), a random primer labeling kit, using mouse p38α or p38β cDNA as a template. A glyceraldehyde 3-phosphate dehydrogenase (G3PDH) probe was purchased from Clontech (Palo Alto, Calif.), Catalog Number 9805-1. The fragments were purified from low-melting temperature agarose, as described in Maniatis, T., et al., *Molecular Cloning: A Laboratory Manual,* 1989. The G3PDH probe was labeled with REDIVUE™ $^{32}$P-dCTP (Amersham Pharmacia Biotech, Piscataway, N.J.) and Strip-EZ labelling kit (Ambion, Austin, Tex.). mRNA was quantitated by a PhosphoImager (Molecular Dynamics, Sunnyvale, Calif.).

TABLE 1

Nucleotide Sequences of Human p38α Chimeric (deoxy gapped) Phosphorothioate Oligonucleotides

| ISIS NO. | NUCLEOTIDE SEQUENCE[1] (5' -> 3') | TARGET SEQ ID NO. | GENE NUCLEOTIDE CO-ORDINATES[2] | GENE TARGET REGION |
|---|---|---|---|---|
| 16486 | AAGACCGGGCCCGGAATTCC | 3 | 0001–0020 | 5'-UTR |
| 16487 | GTGGAGGCCAGTCCCCGGGA | 4 | 0044–0063 | 5'-UTR |
| 16488 | TGGCAGCAAAGTGCTGCTGG | 5 | 0087–0106 | 5'-UTR |
| 16489 | CAGAGAGCCTCCTGGGAGGG | 6 | 0136–0155 | 5'-UTR |
| 16490 | TGTGCCGAATCTCGGCCTCT | 7 | 0160–0179 | 5'-UTR |
| 16491 | GGTCTCGGGCGACCTCTCCT | 8 | 0201–0220 | 5'-UTR |
| 16492 | CAGCCGCGGGACCAGCGGCG | 9 | 0250–0269 | 5'-UTR |
| 16493 | CATTTTCCAGCGGCAGCCGC | 10 | 0278–0297 | AUG |
| 16494 | TCCTGAGACATTTTCCAGCG | 11 | 0286–0305 | AUG |
| 16495 | CTGCCGGTAGAACGTGGGCC | 12 | 0308–0327 | coding |
| 16496 | GTAAGCTTCTGACATTTCAC | 13 | 0643–0662 | coding |
| 16497 | TTTAGGTCQCTGTGAATTAT | 14 | 0798–0817 | coding |
| 16498 | ATGTTCTTCCAGTCAACAGC | 15 | 0939–0958 | coding |
| 16499 | TAAGGAGGTCCCTGCTTTCA | 16 | 1189–1208 | coding |
| 16500 | AACCAGGTGCTCAGGACTCC | 17 | 1368–1387 | stop |
| 16501 | GAAGTGGGATCAACAGAACA | 18 | 1390–1409 | 3'-UTR |
| 16502 | TGAAAAGGCCTTCCCCTCAC | 19 | 1413–1432 | 3'-UTR |
| 16503 | AGGCACTTGAATAATATTTG | 20 | 1444–1463 | 3'-UTR |
| 16504 | CTTCCACCATGGAGGAAATC | 21 | 1475–1494 | 3'-UTR |
| 16505 | ACACATGCACACACACTAAC | 22 | 1520–1539 | 3'-UTR |

[1]Emboldened residues, 2'-methoxyethoxy- residues (others are 2'-deoxy-) including "C" residues, 5-methyl-cytosine all linkages are phosphorothioate linkages.
[2]Co-ordinates from Genbank Accession No. L35253, locus name "HUMMAPKNS", SEQ ID NO. 1.

For an initial screen of human p38α antisense oligonucleotides, Jurkat cells were electroporated with 10 μM oligonucleotide. mRNA was measured by Northern blot. Results are shown in Table 2. Oligonucleotides 16496 (SEQ ID NO. 13), 16500 (SEQ ID NO. 17) and 16503 (SEQ ID NO. 20) gave 35% or greater inhibition of p38α mRNA.

TABLE 2

Inhibition of Human p38α mRNA expression in Jurkat Cells by Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| control | — | — | 100% | 0% |
| 16486 | 3 | 5'-UTR | 212% | — |
| 16487 | 4 | 5'-UTR | 171% | — |
| 16488 | 5 | 5'-UTR | 157% | — |
| 16489 | 6 | 5'-UTR | 149% | — |
| 16490 | 7 | 5'-UTR | 152% | — |
| 16491 | 8 | 5'-UTR | 148% | — |
| 16492 | 9 | 5'-UTR | 125% | — |
| 16493 | 10 | AUG | 101% | — |
| 16494 | 11 | AUG | 72% | 28% |
| 16495 | 12 | coding | 72% | 28% |
| 16496 | 13 | coding | 61% | 39% |
| 16497 | 14 | coding | 104% | — |
| 16498 | 15 | coding | 88% | 12% |
| 16499 | 16 | coding | 74% | 26% |
| 16500 | 17 | stop | 63% | 37% |
| 16501 | 18 | 3'-UTR | 77% | 23% |
| 16502 | 19 | 3'-UTR | 79% | 21% |
| 16503 | 20 | 3'-UTR | 65% | 35% |
| 16504 | 21 | 3'-UTR | 72% | 28% |
| 16505 | 22 | 3'-UTR | 93% | 7% |

The most active human p38α oligonucleotides were chosen for dose response studies. Oligonucleotide 16490 (SEQ ID NO. 7) which showed no inhibition in the initial screen was included as a negative control. Jurkat cells were grown and treated as described above except the concentration of oligonucleotide was varied as indicated in Table 3. Results are shown in Table 3. Each of the active oligonucleotides showed a dose response effect with $IC_{50}$s around 10 nM. Maximum inhibition was approximately 70% with 16500 (SEQ ID NO. 17). The most active oligonucleotides were also tested for their ability to inhibit p38β. None of these oligonucleotides significantly reduced p38β mRNA expression.

TABLE 3

Dose Response of p38α mRNA in Jurkat cells to human p38α Chimeric (deoxy gapped) Phosphorothioate Oligonucleotides

| ISIS # | SEQ ID NO: | ASO Gene Target | Dose | % mRNA Expression | % mRNA Inhibition |
|---|---|---|---|---|---|
| control | — | — | — | 100% | 0% |
| 16496 | 13 | coding | 2.5 nM | 94% | 6% |
| " | " | " | 5 nM | 74% | 26% |
| " | " | " | 10 nM | 47% | 53% |
| " | " | " | 20 nM | 41% | 59% |
| 16500 | 17 | stop | 2.5 nM | 82% | 18% |
| " | " | " | 5 nM | 71% | 29% |
| " | " | " | 10 nM | 49% | 51% |
| " | " | " | 20 nM | 31% | 69% |
| 16503 | 20 | 3'-UTR | 2.5 nM | 74% | 26% |
| " | " | " | 5 nM | 61% | 39% |
| " | " | " | 10 nM | 53% | 47% |
| " | " | " | 20 nM | 41% | 59% |
| 16490 | 7 | 5'-UTR | 2.5 nM | 112% | — |
| " | " | " | 5 nM | 109% | — |
| " | " | " | 10 nM | 104% | — |
| " | " | " | 20 nM | 97% | 3% |

Example 3: Human p38β Oligonucleotide Sequences

Antisense oligonucleotides were designed to target human p38β. Target sequence data are from the p38β MAPK cDNA sequence; Genbank accession number U53442, provided herein as SEQ ID NO: 23. Oligonucleotides was synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines were 5-methyl-cytosines. These oligonucleotide sequences are shown in Table 4.

TABLE 4

Nucleotide Sequences of Human p38β Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 17891 | CGACATGTCCGGAGCAGAAT | 25 | 0006-0025 | AUG |
| 17892 | TTCAGCTCCTGCCGGTAGAA | 26 | 0041-0060 | coding |
| 17893 | TGCGGCACCTCCCACACGGT | 27 | 0065-0084 | coding |
| 17894 | CCGAACAGACGGAGCCGTAT | 28 | 0121-0140 | coding |
| 17895 | GTGCTTCAGGTGCTTGAGCA | 29 | 0240-0259 | coding |
| 17896 | GCGTGAAGACGTCCAGAAGC | 30 | 0274-0293 | coding |
| 17897 | ACTTGACGATGTTGTTCAGG | 31 | 0355-0374 | coding |
| 17898 | AACGTGCTCGTCAAGTGCCA | 32 | 0405-0424 | coding |
| 17899 | ATCCTGAGCTCACAGTCCTC | 33 | 0521-0540 | coding |
| 17900 | ACTGTTTGGTTGTAATGCAT | 34 | 0635-0654 | coding |
| 17901 | ATGATGCGCTTCAGCTGGTC | 35 | 0731-0750 | coding |
| 17902 | GCCAGTGCCTCAGCTGCACT | 36 | 0935-0954 | coding |
| 17903 | AACGCTCTCATCATATGGCT | 37 | 1005-1024 | coding |
| 17904 | CAGCACCTCACTGCTCAATC | 38 | 1126-1145 | stop |
| 17905 | TCTGTGACCATAGGAGTGTG | 39 | 1228-1247 | 3'-UTR |

TABLE 4-continued

Nucleotide Sequences of Human p38β
Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 17906 | ACACATGTTTGTGCATGCAT | 40 | 1294-1313 | 3'-UTR |
| 17907 | CCTACACATGGCAAGCACAT | 41 | 1318-1337 | 3'-UTR |
| 17908 | TCCAGGCTGAGCAGCTCTAA | 42 | 1581-1600 | 3'-UTR |
| 17909 | AGTGCACGCTCATCCACACG | 43 | 1753-1772 | 3'-UTR |
| 17910 | CTTGCCAGATATGGCTGCTG | 44 | 1836-1855 | 3'-UTR |

[1]Emboldened residues, 2'-methoxyethoxy- residues (others are 2'-deoxy-) including "C" residues, 5-methyl-cytosines; all linkages are phosphorothioate linkages.
[2]Co-ordinates from Genbank Accession No. U53442, locus name "HSU53442", SEQ ID NO. 23.

For an initial screen of human p38β antisense oligonucleotides, HUVEC cells were cultured and treated as described in Example 2. mRNA was measured by Northern blot as described in Example 2. Results are shown in Table 5. Every oligonucleotide tested gave at least 50% inhibition. Oligonucleotides 17892 (SEQ ID NO. 26), 17893 (SEQ ID NO. 27), 17894 (SEQ ID NO. 28), 17899 (SEQ ID NO. 33), 17901 (SEQ ID NO. 35), 17903 (SEQ ID NO. 37), 17904 (SEQ ID NO. 38), 17905 (SEQ ID NO. 39), 17907 (SEQ ID NO. 41), 17908 (SEQ ID NO. 42), and 17909 (SEQ ID NO. 43) gave greater than approximately 85% inhibition.

TABLE 5

Inhibition of Human p38β mRNA expression in HUVEC Cells by Chimeric (deoxy gapped) Phosphorothioate Oligonucleotides

| ISIS No: | SEQ ID NO: | GENE TARGET REGION | % mRNA EXPRESSION | % mRNA EXPRESSION |
|---|---|---|---|---|
| control | — | — | 100% | 0% |
| 17891 | 25 | AUG | 22% | 78% |
| 17892 | 26 | coding | 10% | 90% |
| 17893 | 27 | coding | 4% | 96% |
| 17894 | 28 | coding | 13% | 87% |
| 17895 | 29 | coding | 25% | 75% |
| 17896 | 30 | coding | 24% | 76% |
| 17897 | 31 | coding | 25% | 75% |
| 17898 | 32 | coding | 49% | 51% |
| 17899 | 33 | coding | 5% | 95% |
| 17900 | 34 | coding | 40% | 60% |
| 17901 | 35 | coding | 15% | 85% |
| 17902 | 36 | coding | 49% | 51% |
| 17903 | 37 | coding | 11% | 89% |
| 17904 | 38 | stop | 9% | 91% |
| 17905 | 39 | 3'-UTR | 14% | 86% |
| 17906 | 40 | 3'-UTR | 22% | 78% |
| 17907 | 41 | 3'-UTR | 8% | 92% |
| 17908 | 42 | 3'-UTR | 17% | 83% |
| 17909 | 43 | 3'-UTR | 13% | 87% |
| 17910 | 44 | 3'-UTR | 26% | 74% |

Oligonucleotides 17893 (SEQ ID NO. 27), 17899 (SEQ ID NO. 33), 17904 (SEQ ID NO. 38), and 17907 (SEQ ID NO. 41) were chosen for dose response studies. HUVEC cells were cultured and treated as described in Example 2 except that the oligonucleotide concentration was varied as shown in Table 6. The Lipofectin®/Oligo ratio was maintained at 3 µg Lipofectin®/100 nM oligo per ml. mRNA was measured by Northern blot as described in Example 2.

Results are shown in Table 6. Each oligonucleotide tested had an $IC_{50}$ of less than 10 nM. The effect of these oligonucleotides on human p38α was also determined. Only oligonucleotide 17893 (SEQ ID NO. 27) showed an effect on p38α mRNA expression. The $IC_{50}$ of this oligonucleotide was approximately 4 fold higher for p38α compared to p38β.

TABLE 6

Dose Response of p38β in Huvec cells to human p38β Chimeric (deoxy gapped) Phosphorothioate Oligonucleotides

| ISIS # | SEQ ID NO: | ASO Gene Target | Dose | % mRNA Expression | % mRNA Inhibition |
|---|---|---|---|---|---|
| control | — | — | — | 100% | 0% |
| 17893 | 27 | coding | 10 nM | 37% | 63% |
| " | " | " | 25 nM | 18% | 82% |
| " | " | " | 50 nM | 16% | 84% |
| " | " | " | 100 nM | 19% | 81% |
| 17899 | 33 | coding | 10 nM | 37% | 63% |
| " | " | " | 25 nM | 23% | 77% |
| " | " | " | 50 nM | 18% | 82% |
| " | " | " | 100 nM | 21% | 79% |
| 17904 | 38 | stop | 10 nM | 31% | 69% |
| " | " | " | 25 nM | 21% | 79% |
| " | " | " | 50 nM | 17% | 83% |
| " | " | " | 100 nM | 19% | 81% |
| 17907 | 41 | 3'-UTR | 10 nM | 37% | 63% |
| " | " | " | 25 nM | 22% | 78% |
| " | " | " | 50 nM | 18% | 72% |
| " | " | " | 100 nM | 18% | 72% |

Example 4: Rat p38α Oligonucleotide Sequences

Antisense oligonucleotides were designed to target rat p38α. Target sequence data are from the p38 MAPK cDNA sequence; Genbank accession number U73142, provided herein as SEQ ID NO: 45. Oligonucleotides was synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages in the wings are phosphodiester (P=O). Internucleoside linkages in the central gap are phosphorothioate (P=S). All 2'-MOE cytosines and 2'-OH cytosines were 5-methyl-cytosines. These oligonucleotide sequences are shown in Table 7.

bEND.3, a mouse endothelial cell line (gift of Dr. Werner Risau; see Montesano et al., *Cell,* 1990, 62, 435, and Stepkowski et al., *J. Immunol.,* 1994, 153, 5336) were grown in high-glucose DMEM (Life Technologies, Gaithersburg, Md.) medium containing 10% fetal bovine serum (FBS) and 1% Penicillin/Streptomycin. Cells were plated at approximately 2×10⁵ cells per 100 mm dish. Within 48 hours of plating, the cells were washed with phosphate-buffered saline (Life Technologies). Then, Opti-MEM® medium containing 3 µg/mL LIPOFECTIN® and an appropriate amount of oligonucleotide were added to the cells. As a control, cells were treated with LIPOFECTIN® without oligonucleotide under the same conditions and for the same times as the oligonucleotide-treated samples.

After 4 hours at 37° C., the medium was replaced with high glucose DMEM medium containing 10% FBS and 1% Penicillin/Streptomycin. The cells were typically allowed to recover overnight (about 18 to 24 hours) before RNA and/or protein assays were performed as described in Example 2. The p38α, p38β and G3PDH probes used were identical to those described in Example 2.

TABLE 7

Nucleotide Sequences of Rat p38α Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 21844 | CoToGoCoGsAsCsAsTsTsTsTsCsCsAsGoCoGoGoC | 47 | 0001-0020 | AUG |
| 21845 | GoGoToAoAsGsCsTsTsCsTsGsAsCsAsCoToToCoA | 48 | 0361-0380 | coding |
| 21846 | GoGoCoCoAsGsAsGsAsCsTsGsAsAsTsGoToAoGoT | 49 | 0781-0800 | coding |
| 21871 | CoAoToCoAsTsCsAsGsGsGsTsCsGsTsGoGoToAoC | 50 | 0941-0960 | coding |
| 21872 | GoGoCoAoCsAsAsAsGsCsTsAsAsTsGsAoCoToToC | 51 | 1041-1060 | coding |
| 21873 | AoGoGoToGsCsTsCsAsGsGsAsCsTsCsCoAoToToT | 52 | 1081-1100 | stop |
| 21874 | GoGoAoToGsGsAsCsAsGsAsASCsAsGsAoAoGoCoA | 53 | 1101-1120 | 3'-UTR |
| 21875 | GoAoGoCoAsGsGsCsAsGsAsCsTsGsCsCoAoAoGoG | 54 | 1321-1340 | 3'-UTR |
| 21876 | AoGoGoCoTsAsGsAsGsCsCsCsAsGsGsAoGoCoCoA | 55 | 1561-1580 | 3'-UTR |
| 21877 | GoAoGoCoCsTsGsTsGsCsCsTsGsGsCsAoCoToGoG | 56 | 1861-1880 | 3'-UTR |
| 21878 | ToGoCoAoCsCsAsCsAsAsGsCsAsCsCsToGoGoAoG | 57 | 2081-2100 | 3'-UTR |
| 21879 | GoGoCoToAsCsCsAsTsGsAsGsTsGsAsGoAoAoGoA | 58 | 2221-2240 | 3'-UTR |
| 21880 | GoToCoCoCsTsGsCsAsCsTsGsAsTsAsGoAoGoAoA | 59 | 2701-2720 | 3'-UTR |
| 21881 | ToCoToToCsAsAsTsGsGsAsGsAsAsAoCoToGoG | 60 | 3001-3020 | 3'-UTR |

[1]Emboldened residues, 2'-methoxyethoxy- residues (others are 2'-deoxy-); 2'-MOE cytosines and 2'-deoxy cytosine residues are 5-methyl-cytosines; "s" linkages are phosphorothioate linkages; "o" linkages are phosphodiester linkages.
[2]Co-ordinates from Genbank Accession No. U73142, locus name "RNU73142", SEQ ID NO. 45.

Rat p38α antisense oligonucleotides were screened in bEND.3 cells for inhibition of p38α and p38β mRNA expression. The concentration of oligonucleotide used was 100 nM. Results are shown in Table 8. Oligonucleotides 21844 (SEQ ID NO. 47), 21845 (SEQ ID NO. 48), 21872 (SEQ ID NO. 51), 21873 (SEQ ID NO. 52), 21875 (SEQ ID NO. 54), and 21876 (SEQ ID NO. 55) showed greater than approximately 70% inhibition of p38α mRNA with minimal effects on p38β mRNA levels. Oligonucleotide 21871 (SEQ ID NO. 50) inhibited both p38α and p38β levels greater than 70%.

TABLE 8

Inhibition of Mouse p38 mRNA expression in bEND.3 Cells by Chimeric (deoxy gapped) Mixed Backbone p38α Antisense Oligonucleotides

| ISIS No: | SEQ ID NO: | GENE TARGET REGION | % p38α mRNA INHIBITION | % p38β mRNA INHIBITION |
|---|---|---|---|---|
| control | — | 13 | 0% | 0% |
| 21844 | 47 | AUG | 81% | 20% |
| 21845 | 48 | coding | 75% | 25% |
| 21871 | 50 | coding | 90% | 71% |
| 21872 | 51 | coding | 87% | 23% |
| 21873 | 52 | stop | 90% | 3% |
| 21874 | 53 | 3'-UTR | 38% | 21% |
| 21875 | 54 | 3'-UTR | 77% | — |
| 21876 | 55 | 3'-UTR | 69% | — |
| 21877 | 56 | 3'-UTR | 55% | 13% |
| 21878 | 57 | 3'-UTR | 25% | 10% |
| 21879 | 58 | 3'-UTR | — | — |
| 21881 | 60 | 3'-UTR | — | — |

Several of the most active oligonucleotides were selected for dose response studies. bEND.3 cells were cultured and treated as described above, except that the concentration of oligonucleotide was varied as noted in Table 9. Results are shown in Table 9.

TABLE 9

Dose Response of bEND.3 cells to rat p38β
Chimeric (deoxy gapped) Phosphorothioate Oligonucleotides

| ISIS # | SEQ ID NO: | ASO Gene Target | Dose | % p38α mRNA Inhibition | % p38β mRNA Inhibition |
|---|---|---|---|---|---|
| control | — | — | — | 100% | 0% |
| 21844 | 47 | AUG | 1 nM | — | — |
| " | " | " | 5 nM | — | — |
| " | " | " | 25 nM | 36% | 8% |
| " | " | " | 100 nM | 80% | 5% |
| 21871 | 50 | coding | 1 nM | 1% | — |
| " | " | " | 5 nM | 23% | 4% |
| " | " | " | 25 nM | 34% | 24% |
| " | " | " | 100 nM | 89% | 56% |
| 21872 | 51 | stop | 1 nM | — | — |
| " | " | " | 5 nM | — | — |
| " | " | " | 25 nM | 35% | — |
| " | " | " | 100 nM | 76% | 1% |
| 21873 | 52 | stop | 1 nM | — | 53% |
| " | " | " | 5 nM | — | 31% |
| " | " | " | 25 nM | 54% | 28% |
| " | " | " | 100 nM | 92% | 25% |
| 21875 | 54 | 3'-UTR | 1 nM | — | 11% |
| " | " | " | 5 nM | — | 16% |
| " | " | " | 25 nM | 33% | 2% |
| " | " | " | 100 nM | 72% | 4% |

Example 5: Mouse p38β Oligonucleotide Sequences

Antisense oligonucleotides were designed to target mouse p38β. Target sequence data are from a mouse EST sequence; Genbank accession number AI119044, provided herein as SEQ ID NO: 61. Oligonucleotides was synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages in the wings are phosphodiester (P=O). Internucleoside linkages in the central gap are phosphorothioate (P=S). All 2'-MOE cytosines and 2'-OH cytosines were 5-methyl-cytosines. These oligonucleotide sequences are shown in Table 10.

TABLE 10

Nucleotide Sequences of Mouse p38β
Chimeric (deoxy gapped) Phosphorothioate Oligonucleotides

| ISIS NO. | NUCLEOTIDE SEQUENCE[1] (5' -> 3') | SEQ ID NUCLEOTIDE NO: | TARGET GENE CO-ORDINATES[2] |
|---|---|---|---|
| 100800 | CoAoCoAoGsAsAsGsCsAsGsCsTsGsGsAoGoCoGoA | 63 | 0051-0070 |
| 100801 | ToGoCoGoGsCsAsCsCsTsCsCsCsAsTsAoCoToGoT | 64 | 0119-0138 |
| 100802 | CoCoCoToGsCsAsGsCsCsGsCsTsGsCsGoGoCoAoC | 65 | 0131-0150 |
| 100803 | GoCoAoGoAsCsTsGsAsGsCsCsGsTsAsGoGoCoGoC | 66 | 0171-0190 |
| 100804 | ToToAoCoAsGsCsCsAsAsCsCsTsTsCsToGoGoCoGoC | 67 | 0211-0230 |
| 100805 | GoToAoToGsTsCsCsTsCsCsTsCsGsCsGoToGoGoA | 68 | 0261-0280 |
| 100806 | AoToGoGoAsTsGsTsGsGsCsCsGsGsCsGoToGoAoA | 69 | 0341-0360 |
| 100807 | GoAoAoToTsGsAsAsCsAsTsGsCsTsCsAoToCoGoC | 70 | 0441-0460 |
| 100808 | AoCoAoToTsGsCsTsGsGsGsCsTsTsCsAoGoGoToC | 71 | 0521-0540 |
| 100809 | AoToCoCoTsCsAsGsCsTsCsGsCsAsGsToCoCoToC | 72 | 0551-0570 |
| 100810 | ToAoCoCoAsCsCsGsTsGsTsGsGsCsCsAoCoAoToA | 73 | 0617-0636 |
| 100811 | CoAoGoToTsTsAsGsCsAsTsGsAsTsCsToCoToGoG | 74 | 0644-0663 |
| 100812 | CoAoGoGoCsCsAsCsAsGsAsCsCsAsGsAoToGoToC | 75 | 0686-0705 |
| 100813 | CoCoToToCsCsAsGsCsAsGsTsTsCsAsAoGoCoCoA | 76 | 0711-0730 |
| 101123 | CoAoGoCoAsCsCsAsTsGsGsAsCsGsCsGoGoAoAoC | 77 | 21671 mismatch |

[1] Emboldened residues, 2'-methoxyethoxy- residues (others are 2'-deoxy-), including 2'-MOE and 2'-deoxy residues, 5-methyl-cytosines; "s" linkages are phosphorothioate linkages "o" linkages are phosphodiester.
[2] Co-ordinates from Genbank Accession No. AI119044, locus name "AI119044", SEQ ID NO. 61.

Mouse p38β antisense sequences were screened in bEND.3 cells as described in Example 4. Results are shown in Table 11.

Oligonucleotides 100800 (SEQ ID NO. 63), 100801 (SEQ ID NO. 64), 100803 (SEQ ID NO. 66), 100804 (SEQ ID NO. 67), 100805 (SEQ ID NO. 68), 100807 (SEQ ID NO. 70), 100808 (SEQ ID NO. 71), 100809 (SEQ ID NO. 72), 100810 (SEQ ID NO. 73), 100811 (SEQ ID NO. 74), and 100813 (SEQ ID NO. 76) resulted in at least 50% inhibition of p38β mRNA expression. Oligonucleotides 100801 (SEQ ID NO. 64), 100803 (SEQ ID NO. 66), 100804 (SEQ ID NO. 67), 100805 (SEQ ID NO. 68), 100809 (SEQ ID NO. 72), and 100810 (SEQ ID NO. 73) resulted in at least 70% inhibition. Oligonucleotides 100801 (SEQ ID NO. 64), 100805 (SEQ ID NO. 68), and 100811 (SEQ ID NO. 74) resulted in significant inhibition of p38β mRNA expression in addition to their effects on p38β.

TABLE 11

Inhibition of Mouse p38 mRNA expression in bEND.3 Cells by Chimeric (deoxy gapped) Mixed Backbone p38β Antisense Oligonucleotides

| ISIS No: | SEQ ID NO: | % p38β mRNA INHIBITION | % p38α mRNA INHIBITION |
|---|---|---|---|
| control | — | 0% | 0% |
| 100800 | 63 | 51% | — |
| 100801 | 64 | 74% | 31% |
| 100802 | 65 | 35% | — |
| 100803 | 66 | 74% | 18% |
| 100804 | 67 | 85% | 18% |
| 100805 | 68 | 78% | 58% |
| 100806 | 69 | 22% | 3% |
| 100807 | 70 | 64% | — |
| 100808 | 71 | 53% | 13% |
| 100809 | 72 | 84% | 14% |
| 100810 | 73 | 72% | 1% |
| 100811 | 74 | 60% | 43% |
| 100812 | 75 | 36% | 17% |
| 100813 | 76 | 54% | — |

Example 6: Effect of p38 MAPK Antisense Oligonucleotides on IL-6 Secretion p38 MAPK antisense oligonucleotides were tested for their ability to reduce IL-6 secretion. bEND.3 cells were cultured and treated as described in Example 4 except that 48 hours after oligonucleotide treatment, cells were stimulated for 6 hours with 1 ng/mL recombinant mouse IL-1 (R&D Systems, Minneapolis, Minn.). IL-6 was measured in the medium using an IL-6 ELISA kit (Endogen Inc., Woburn, Mash.).

Results are shown in Table 13. Oligonucleotides targeting a specific p38 MAPK isoform were effective in reducing IL-6 secretion greater than approximately 50%.

TABLE 13

Effect of p38 Antisense Oligonucleotides on IL-6 secretion

| ISIS No: | SEQ ID NO: | GENE TARGET | DOSE (μM) | % IL-6 INHIBITION |
|---|---|---|---|---|
| control | — | — | | 0% |
| 21873 | 52 | p38α | 100 | 49% |
| 100804 | 67 | p38β | 100 | 57% |
| 21871 | 50 | p38α and p38β | 200 | 23% |

Example 7: Activity of p38α Antisense Oligonucleotides in Rat Cardiomyocytes

Rat p38α antisense oligonucleotides were screened in Rat A-10 cells. A-10 cells (American Type Culture Collection, Manassas, Va.) were grown in high-glucose DMEM (Life Technologies, Gaithersburg, Md.) medium containing 10% fetal calf serum (FCS). Cells were treated with oligonucleotide as described in Example 2. Oligonucleotide concentration was 200 nM. mRNA was isolated 24 hours after time zero and quantitated by Northern blot as described in Example 2.

Results are shown in Table 14. Oligonucleotides 21845 (SEQ ID NO. 48), 21846 (SEQ ID NO. 49), 21871 (SEQ ID NO. 50), 21872 (SEQ ID NO. 51), 21873 (SEQ ID NO. 52), 21874 (SEQ ID NO. 53), 21875 (SEQ ID NO. 54), 21877 (SEQ ID NO. 56), 21878 (SEQ ID NO. 57), 21879 (SEQ ID NO. 58), and 21881 (SEQ ID NO. 60) inhibited p38α mRNA expression by 65% or greater in this assay. Oligonucleotides 21846 (SEQ ID NO. 49), 21871 (SEQ ID NO. 50), 21872 (SEQ ID NO. 51), 21877 (SEQ ID NO. 56), and 21879 (SEQ ID NO. 58) inhibited p38α mRNA expression by greater than 85%.

TABLE 14

Inhibition of Rat p38α mRNA expression in A-10 Cells by Chimeric (deoxy gapped) Mixed Backbone p38α Antisense Oligonucleotides

| ISIS No: | SEQ ID NO: | GENE TARGET REGION | % p38α mRNA EXPRESSION | % p38α mRNA INHIBITION |
|---|---|---|---|---|
| control | — | — | 100% | 0% |
| 21844 | 47 | AUG | 75% | 25% |
| 21845 | 48 | coding | 25% | 75% |
| 21846 | 49 | coding | 8% | 92% |
| 21871 | 50 | coding | 12% | 88% |
| 21872 | 51 | coding | 13% | 87% |
| 21873 | 52 | stop | 19% | 81% |
| 21874 | 53 | 3'-UTR | 22% | 78% |
| 21875 | 54 | 3'-UTR | 26% | 74% |
| 21876 | 55 | 3'-UTR | 61% | 39% |
| 21877 | 56 | 3'-UTR | 12% | 88% |
| 21878 | 57 | 3'-UTR | 35% | 65% |
| 21879 | 58 | 3'-UTR | 11% | 89% |
| 21881 | 60 | 3'-UTR | 31% | 69% |

The most active oligonucleotide in this screen (SEQ ID NO. 49) was used in rat cardiac myocytes prepared from neonatal rats (Zechner, D., et. al., J. Cell Biol., 1997, 139, 115–127). Cells were grown as described in Zechner et al. and transfected with oligonucleotide as described in Example 2. Oligonucleotide concentration was 1 μM. mRNA was isolated 24 hrs after time zero and quantitated using Northern blotting as described in Example 2. An antisense oligonucleotide targeted to JNK-2 was used as a non-specific target control.

Results are shown in Table 15. Oligonucleotide 21846 (SEQ ID NO. 49) was able to reduce p38α expression in rat cardiac myocytes by nearly 60%. The JNK-2 antisense oligonucleotide had little effect on p38α expression.

TABLE 15

Inhibition of Rat p38α mRNA expression in Rat Cardiac Myocytes by a Chimeric (deoxy gapped) Mixed Backbone p38α Antisense Oligonucleotide

| ISIS No: | SEQ ID NO: | GENE TARGET REGION | % p38α mRNA EXPRESSION | % p38α mRNA INHIBITION |
|---|---|---|---|---|
| control | — | — | 100% | 0% |
| 21846 | 49 | coding | 41% | 59% |

Example 8: Additional Human p38α Oligonucleotide Sequences

Additional antisense oligonucleotides were designed to target human p38α based on active rat sequences. Target sequence data are from the p38 MAPK cDNA sequence; Genbank accession number L35253, provided herein as SEQ ID NO: 1. Oligonucleotides was synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines and 2'-OH cytosines were 5-methyl-cytosines. These oligonucleotide sequences are shown in Table 16.

TABLE 16

Additional Nucleotide Sequences of Human p38α Chimeric (deoxy gapped) Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 100860 | CTGAGACATTTTCCAGCGGC | 78 | 0284-0303 | AUG |
| 100861 | ACGCTCGGGCACCTCCCAGA | 79 | 0344-0363 | coding |
| 100862 | AGCTTCTTCACTGCCACACG | 80 | 0439-0458 | coding |
| 100863 | AATGATGGACTGAAATGGTC | 81 | 0464-0483 | coding |
| 100864 | TCCAACAGACCAATCACATT | 82 | 0538-0557 | coding |
| 100865 | TGTAAGCTTCTGACATTTCA | 83 | 0644-0663 | coding |
| 100866 | TGAATGTATATACTTTAGAC | 84 | 0704-0723 | coding |
| 100867 | CTCACAGTCTTCATTCACAG | 85 | 0764-0783 | coding |
| 100868 | CACGTAGCCTGTCATTTCAT | 86 | 0824-0843 | coding |
| 100869 | CATCCCACTGACCAAATATC | 87 | 0907-0926 | coding |
| 100870 | TATGGTCTGTACCAGGAAAC | 88 | 0960-0979 | coding |
| 100871 | AGTCAAAGACTGAATATAGT | 89 | 1064-1083 | coding |
| 100872 | TTCTCTTATCTGAGTCCAAT | 90 | 1164-1183 | coding |
| 100873 | CATCATCAGGATCGTGGTAC | 91 | 1224-1243 | coding |
| 100874 | TCAAAGGACTGATCATAAGG | 92 | 1258-1277 | coding |
| 100875 | GGCACAAAGCTGATGACTTC | 93 | 1324-1343 | coding |
| 100876 | AGGTGCTCAGGACTCCATCT | 94 | 1364-1383 | stop |
| 100877 | GCAACAAGAGGCACTTGAAT | 95 | 1452-1471 | 3'-UTR |

[1]Emboldened residues, 2'-methoxyethoxy- residues (others are 2'-deoxy-) including "C" and "C" residues, 5-methyl-cytosines; all linkages are phosphorothioate linkages.
[2]Co-ordinates from Genbank Accession No. L35253, locus name "HUMMAPKNS", SEQ ID NO. 1.

What is claimed is:

1. An antisense compound 8 to 30 nucleobases in length targeted to the 5-untranslated region, translational start site, translational termination region or 3'-untranslated region of a nucleic acid molecule encoding a p38 mitogen activated protein kinase, wherein said antisense compound inhibits the expression of said p38 mitogen activated protein kinase.

2. The antisense compound of claim 1 which is an antisense oligonucleotide.

3. The antisense compound of claim 2 wherein the antisense oligonucleotide comprises at least an 8-nucleobase portion of SEQ ID NO: 17, 20, 38, 39, 41, 42 or 43.

4. The antisense compound of claim 2 wherein the antisense oligonucleotide comprises at least one modified internucleoside linkage.

5. The antisense compound of claim 4 wherein the modified internucleoside linkage is a phosphorothioate linkage.

6. The antisense compound of claim 2 wherein the antisense oligonucleotide comprises at least one modified sugar moiety.

7. The antisense compound of claim 6 wherein the modified sugar moiety is a 2'-O-methoxyethyl moiety.

8. The antisense compound of claim 2 wherein the antisense oligonucleotide comprises at least one modified nucleobase.

9. The antisense compound of claim 8 wherein modified nucleobase is a 5-methyl cytosine.

10. The antisense compound of claim 2 wherein the antisense oligonucleotide is a chimeric oligonucleotide.

11. A method of inhibiting the expression of a p38 mitogen activated protein kinase in cells or tissues comprising contacting said cells or tissue in vitro with the antisense compound of claim 1 so that expression of said p38 mitogen activated protein kinase is inhibited.

12. An antisense compound 8 to 30 nucleobases in length targeted to the coding region of a nucleic acid molecule encoding a p38 mitogen-activated protein kinase, wherein said antisense compound inhibits the expression of said p38 mitogen-activated protein kinase and comprises at least an 8-nucleobase portion of SEQ ID NO: 13, 27, 28, 33, 35 or 37.

13. The antisense compound of claim 12 which is an antisense oligonucleotide.

14. The antisense compound of claim 13 wherein the antisense oligonucleotide comprises at least one modified internucleoside linkage.

15. The antisense compound of claim 14 wherein the modified internucleoside linkage is a phosphorothioate linkage.

16. The antisense compound of claim 13 wherein the antisense oligonucleotide comprises at least one modified sugar moiety.

17. The antisense compound of claim 16 wherein the modified sugar moiety is a 2'-O-methoxyethyl moiety.

18. The antisense compound of claim 13 wherein the antisense oligonucleotide comprises at least one modified nucleobase.

19. The antisense compound of claim 18 wherein modified nucleobase is a 5-methyl cytosine.

20. The antisense compound of claim 20 wherein the antisense oligonucleotide is a chimeric oligonucleotide.

21. A method of inhibiting the expression of a p38 mitogen activated protein kinase in cells or tissues comprising contacting said cells or tissue in vitro with the antisense compound of claim 12 so that expression of said p38 mitogen activated protein kinase is inhibited.

22. An antisense compound 8 to 30 nucleobases in length targeted to p38α mitogen activated protein kinase, wherein said antisense compound inhibits the expression of said p38α mitogen activated protein kinase and does not inhibit the expression of p38β mitogen activated protein kinase by more than 25%.

23. An antisense compound 8 to 30 nucleobases in length targeted to p38β mitogen activated protein kinase, wherein said antisense compound inhibits the expression of said p38β mitogen activated protein kinase and does not inhibit the expression of p38α mitogen activated protein kinase by more than 25%.

24. An antisense compound targeted to the coding region of a nucleic acid molecule encoding a p38 mitogen-activated protein kinase, wherein said antisense compound inhibits the expression of said p38 mitogen-activated protein kinase and consists of SEQ ID NO: 26.

* * * * *

UNITED STATES PATENT AND TRADEMARK OFFICE
CERTIFICATE OF CORRECTION

PATENT NO. : 6,140,124
DATED : October 31, 2000
INVENTOR(S) : Monia et al.

It is certified that error appears in the above-identified patent and that said Letters Patent is hereby corrected as shown below:

At col. 4, line 28, please delete "5°'" and insert -- 5' --.

At col. 4, line 29, please delete "5°'" and insert -- 5' --.

At col. 6, line 34, please delete "815" and insert --8-15--.

At col. 13, line 13, please delete "2'-α-O-trifyl" and insert --2'-β-O-trifyl--.

At col. 25, line 59, please delete "13" and insert -- – --.

At col. 28, Table 10, in heading of second column, please delete "ID".

At col. 28, Table 10, in heading of third column, please delete "NUCLEOTIDE" and insert --ID--.

UNITED STATES PATENT AND TRADEMARK OFFICE
CERTIFICATE OF CORRECTION

PATENT NO. : 6,140,124

DATED : October 31, 2000

INVENTOR(S) : Monia et al.

It is certified that error appears in the above-identified patent and that said Letters Patent is hereby corrected as shown below:

At col. 28, Table 10, in heading of fourth column, please insert --NUCLEOTIDE-- following "GENE".

At col. 28, Table 10, last row, please delete "21671" and insert --21871--.

At col. 28, last line, please delete "A1119044" and insert --AI119044--.

At col. 29, line 16, please delete "p38β" and insert --p38α--.

At col. 29, line 49, please delete "Mash." and insert --MA--.

Signed and Sealed this

Twenty-second Day of May, 2001

Attest:

NICHOLAS P. GODICI

Attesting Officer

Acting Director of the United States Patent and Trademark Office